(12) United States Patent
Gelfman et al.

(10) Patent No.: US 12,370,257 B2
(45) Date of Patent: *Jul. 29, 2025

(54) MATERIALS AND METHODS OF TREATING MHC-I-OPATHY RISK HAPLOTYPES

(71) Applicant: Regeneron Pharmaceuticals, Inc., Tarrytown, NY (US)

(72) Inventors: Sahar Gelfman, Tarrytown, NY (US); Ann Ligocki, Tarrytown, NY (US); Giovanni Coppola, Tarrytown, NY (US); Aris Baras, Tarrytown, NY (US); Arden Moscati, Tarrytown, NY (US); Eli A. Stahl, Tarrytown, NY (US); Jack A. Kosmicki, Tarrytown, NY (US); Manuel Allen Revez Ferreira, Tarrytown, NY (US); Carmelo Romano, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 8 days.

This patent is subject to a terminal disclaimer.

(21) Appl. No.: 17/714,717

(22) Filed: Apr. 6, 2022

(65) Prior Publication Data

US 2022/0323581 A1    Oct. 13, 2022

Related U.S. Application Data

(60) Provisional application No. 63/171,672, filed on Apr. 7, 2021.

(51) Int. Cl.
*A61K 39/395*    (2006.01)
*A61K 31/713*    (2006.01)
(Continued)

(52) U.S. Cl.
CPC ........ *A61K 39/3955* (2013.01); *A61K 31/713* (2013.01); *C07K 16/2833* (2013.01); *C07K 16/40* (2013.01)

(58) Field of Classification Search
CPC .. A61K 39/3955; A61K 31/713; A61K 45/06; A61K 31/7088; C07K 16/2833;
(Continued)

(56) References Cited

U.S. PATENT DOCUMENTS

| 8,969,254 B2 | 3/2015 | Reinherz et al. |
| 9,617,596 B2 | 4/2017 | Comabella et al. |

(Continued)

FOREIGN PATENT DOCUMENTS

| WO | 2012047294 | 4/2012 |
| WO | 2014171800 | 10/2014 |

(Continued)

OTHER PUBLICATIONS

Chen et al. (Ann Rheum Dis 2016;75:916-923).*

(Continued)

*Primary Examiner* — Terra C Gibbs
(74) *Attorney, Agent, or Firm* — Armstrong Teasdale LLP

(57) ABSTRACT

The present disclosure provides methods of treating subjects having an immune disorder by administering to the subject a therapeutically effective amount of an Endoplasmic Reticulum Aminopeptidase 2 (ERAP2) inhibitor in combination with an HLA-A29 or HLA-B27 inhibitory nucleic acid molecule.

13 Claims, 8 Drawing Sheets

Specification includes a Sequence Listing.

(51) Int. Cl.
    *C07K 16/28* (2006.01)
    *C07K 16/40* (2006.01)
(58) Field of Classification Search
    CPC .......... C07K 16/40; C12N 9/485; C12Q 1/00;
                                                C12Q 1/6881
    See application file for complete search history.

(56) References Cited

U.S. PATENT DOCUMENTS

| | | | |
|---|---|---|---|
| 9,907,833 | B2 | 3/2018 | Conrad |
| 10,047,396 | B2 | 8/2018 | Sharp et al. |
| 10,166,210 | B2 | 1/2019 | Pogue-Geile et al. |
| 10,385,398 | B2 | 8/2019 | Hakonarson et al. |
| 10,407,725 | B2 | 9/2019 | Hakonarson et al. |
| 10,927,412 | B2 | 2/2021 | Giudice et al. |
| 2012/0015904 | A1 | 1/2012 | Sharp et al. |
| 2013/0259876 | A1 | 10/2013 | Murphy et al. |
| 2015/0141273 | A1 | 5/2015 | Bosch et al. |
| 2016/0145687 | A1 | 5/2016 | Kallionpaa et al. |
| 2017/0199196 | A1 | 7/2017 | Bosch et al. |
| 2019/0076391 | A1 | 3/2019 | Pogue-Geile et al. |
| 2019/0136322 | A1 | 5/2019 | Kallionpaa et al. |
| 2019/0241633 | A1 | 8/2019 | Fotin-Mleczek et al. |
| 2019/0375842 | A1 | 12/2019 | Drake |
| 2020/0080152 | A1 | 3/2020 | Hakonarson et al. |
| 2021/0002296 | A1 | 1/2021 | Mainolfi et al. |
| 2021/0147799 | A1 | 5/2021 | Zhang et al. |

FOREIGN PATENT DOCUMENTS

| | | |
|---|---|---|
| WO | 2017208001 | 12/2017 |
| WO | 202111376 | 6/2021 |
| WO | 2021113805 | 6/2021 |

OTHER PUBLICATIONS

José A. López de Castro (Frontiers in Immunology, 2018 vol. 9, Article 2463).*
Worth et al. (Curr Treat Options in Rheum (2018) 4:174-182).*
Kuiper et al. (Hum Mol Genet. Nov. 15, 2014; 23(22): 6081-6087).*
Bousquet et al. (J. Clin. Med. 2022, 11, 4772, pp. 1-17).*
Freitas-Neto et al. (Arq Bras Oftalmol. 2015;78(1):56-61).*
Ferenchak et al. (Seminars in Ophthalmology 2021, vol. 36, Nos. 5-6, 452-457).*
Hu et al. (Nucleic Acid Therapeutics, vol. 33, No. 6, 2023, 339-347).*
Alejandro Garanto (Methods in Molecular Biology 2434, 2021 Springer Protocols, Chapter 22, pp. 321-332).*
Vázquez-Domínguez et al. (Nucleic Acids Research, 2024, vol. 52:10447-10463).*
Castro-Santos et al., "ERAP1 and HLA-C interaction in inflammatory bowel disease in the Spanish population", Innate Immunity, 2017, 23(5), pp. 476-481.
Chiaroni-Clarke et al., "Independent confirmation of juvenile idiopathic arthritis genetic risk loci previously identified by immunochip array analysis", Pediatric Rheumatology, 2014, 12(53), pp. 1-4.
Deddouche-Grass et al., "Discovery and Optimization of a Series of Benzofuran Selective ERAP1 Inhibitors: Biochemical and In Silico Studies", ACS Med Chem Lett, 2021, 12, pp. 1137-1142.
Franke et al., "Genome-wide meta-analysis increases to 71 the number of confirmed Crohn's disease susceptibility loci", Nature Genetics, 2010, 42(12), pp. 1118-1126.
Liddle et al., "Targeting the Regulatory Site of ER Aminopeptidase 1 Leads to the Discovery of a Natural Product Modulator of Antigen Presentation", J Med Chem, 2020, 63(6), pp. 3348-3358.
Weglarz-Tomczak et al., "Discovery of potent and selective inhibitors of human aminopeptidases ERAP1 and ERAP2 by screening libraries of phosphorus-containing amino acid and dipeptide analogues", Bioorganic and Medicinal Chemistry Letters, 2016, 26, pp. 4122-4126.
Zervoudi et al., "Rationally designed inhibitor targeting antigentrimming aminopeptidases enhances antigen presentation and cytotoxic T-cell responses", PNAS, 2013, 110(49), pp. 19890-19895.
Van Hout et al., "Exome sequencing and characterization of 49,960 individuals in the UK Biobank", Nature, 2020, 586(7831), pp. 749-756.
Reid et al., "Launching genomics into the cloud: deployment of Mercury, a next generation sequence analysis pipeline", BMC Bioinformatics, 2014, 15(30), pp. 1-11.
Bai et al., "Inference of high resolution HLA types using genome-wide RNA or DNA sequencing reads", BMC Genomics, 2014, 15(325), pp. 1-16.
Robinson et al., "The IPD-IMGT/HLA Database—New developments in reporting HLA variation", Hum Immunol, 2016, 77(3), pp. 233-237.
Jia et al., "Imputing Amino Acid Polymorphisms in Human Leukocyte Antigens", PLOS One, 2013, 8(6), pp. e64683.
Rich et al., "The Type 1 Diabetes Genetics Consortium", Ann NY Acad Sci, 2006, 1079, pp. 1-8.
Delaneau et al., "Accurate, scalable and integrative haplotype estimation", Nature Communications, 2019, 10(5436), pp. 1-10.
Das et al., "Next-generation genotype imputation service and methods", Nat Genet, 2016, 48(10), pp. 1284-1287.
Mbatchou et al., "Computationally efficient whole genome regression for quantitative and binary traits", BioRxiv, 2020, pp. 1-88.
Zhou et al., "Efficiently controlling for case-control imbalance and sample relatedness in large-scale genetic association studies", Nature Genetics, 2018, 50, pp. 1335-1341.
Purcell et al., "PLINK: a tool set for whole-genome association and population-based linkage analyses", Am J Hum Genet, 2007, 81(3), pp. 559-575.
Kuiper et al., "A genome-wide association study identifies a functional ERAP2 haplotype associated with birdshot chorioretinopathy", Hum Mol Genet, 2014, 23(22), pp. 6081-6087.
Kuiper et al., "Functionally distinct ERAP1 and ERAP2 are a hallmark of HLA-A29-(Birdshot) Uveitis", Hum Mol Genet, 2018, 27(24), pp. 4333-4343.
Paladini et al., "An allelic variant in the intergenic region between ERAP1 and ERAP2 correlates with an inverse expression of the two genes", Scientific Reports, 2018, 8(10398), pp. 1-10.
Andres et al., "Balancing Selection Maintains a Form of ERAP2 that Undergoes Nonsense-Mediated Decay and Affects Antigen Presentation", PLOS Genetics, 2010, 6(10), pp. e1001157.
Coulombe-Huntington et al., "Fine-Scale Variation and Genetic Determinants of Alternative Splicing across Individuals", PLOS Genetics, 2009, 5(12), pp. e1000766.
Sanz-Bravo et al., "Allele-specific Alterations in the Peptidome Underlie the Joint Association of HLA-A*29:02 and Endoplasmic Reticulum Aminopeptidase 2 (ERAP2) with Birdshot Chorioretinopathy", Mol Cell Proteomics, 2018, 17(8), pp. 1564-1577.
Yao et al., "Influence of ERAP1 and ERAP2 gene polymorphisms on disease susceptibility in different populations", Human Immunology, 2019, 80(5), pp. 325-334.
Evans et al., "Interaction between ERAP1 and HLA-B27 in ankylosing spondylitis implicates peptide handling in the mechanism for HLA-B27 in disease susceptibility", Nat Genet, 2011, 43(8), pp. 761-767.
Wisniewski et al., "The association of ERAP1 and ERAP2 single nucleotide polymorphisms and their haplotypes with psoriasis vulgaris is dependent on the presence or absence of the HLA-C*06:02 allele and age at disease onset", Hum Immunol, 2018, 79(2), pp. 109-116.
Strange et al., "A genome-wide association study identifies new psoriasis susceptibility loci and an interaction between HLA-C and ERAP1", Nat Genet, 2010, 42(11), pp. 985-990.
Takeuchi et al., "A single endoplasmic reticulum aminopeptidase-1 protein allotype is a strong risk factor for Behçet's disease in HLA-B*51 carriers", Ann Rheum Dis, 2016, 75(12), pp. 2208-2211.
Sanz-Bravo et al., "Ranking the Contribution of Ankylosing Spondylitis-associated Endoplasmic Reticulum Aminopeptidase 1 (ERAP1) Polymorphisms to Shaping the HLA-B*27 Peptidome*", Mol Cell Proteomics, 2018, 17(7), pp. 1308-1323.

(56) References Cited

OTHER PUBLICATIONS

Guasp et al., "The Behçet's disease-associated variant of the aminopeptidase ERAP1 shapes a low-affinity HLA-B*51 peptidome by differential subpeptidome processing", J Biol Chem, 2017, 292(23), pp. 9680-9689.

Mckenzie et al., "Taxonomic hierarchy of HLA class I allele sequences", Genes and Immunity, 1999, 1, pp. 120-129.

Maben et al., "Discovery of Selective Inhibitors of Endoplasmic Reticulum Aminopeptidase 1", J Med Chem, 2020, 63, pp. 103-121.

Georgiadis et al. "Inhibitiors of ER Aminopeptidase 1 and 2: From Design to Clinical Application", Current Medicinal Chemistry, 2019, 26(15), pp. 2715-2729.

De Castro et al., "Molecular and pathogenic effects of endoplasmic reticulum aminopeptidases ERAP1 and ERAP2 in MHC-I-associated inflammatory disorders: Towards a unifying view", Molecular Immunology, 2016, 77, pp. 193-204.

Agrawal et al., "Genetic associations and functional characterization of M1 aminopeptidases and immune-mediated diseases", Genes and Immunity, 2014, 15(8), pp. 521-527.

Dimopoulou et al., "Variant in ERAP1 promoter region is associated with low expression in a patient with a Behcet-like MHC-I-opathy", Journal of Human Genetics, 2019, 65(3), pp. 325-335.

Babaie et al., "The roles of ERAP1 and ERAP2 in autoimmunity and cancer immunity: New insights and perspective", Molecular Immunology, 2020, 121, pp. 7-19.

Non-Final Office Action dated Aug. 22, 2024 in related U.S. Appl. No. 17/384,601.

Kato et al., "Molecular analysis of the serologically defined HLA-AW19 antigens, A genetically distinct family of HLA-A antigens comprising A29, A31, A32, and AW33, but probably not A30", The Journal of Immunology, 1989, 143(10), pp. 3371-3378.

Final Office Action dated Jan. 3, 2025 in related U.S. Appl. No. 17/384,601.

Advisory Action dated Mar. 17, 2025 in related U.S. Appl. No. 17/384,601.

* cited by examiner

| Second HLA-A Allele | UParis (A29 EUR Carriers) | | | GHS cohort #1 (A29 EUR) | | | GHS cohort #2 (A29 EUR) | | | UKB (A29 EUR) | | |
|---|---|---|---|---|---|---|---|---|---|---|---|---|
| | Cases n=286 | Ctrls n=108 | OR (LCI-UCI) | p-val | Carriers n=4014 | OR (LCI-UCI) | p-val | Carriers n=2829 | OR (LCI-UCI) | p-val | Carriers n=38,543 | OR (LCI-UCI) | p-val |
| Aw19 co-susceptible (29,30,31,33) | 41 | 4 | 4.44 (1.55-17.53) | 2.20E-03 | 247 | 2.63 (1.80-3.78) | 1.29E-06 | 184 | 2.69 (1.81-3.92) | 1.07E-06 | 2416 | 2.51 (1.75-3.52) | 9.62E-07 |
| A3002 | 13 | 1 | 5.19 (0.76-222.84) | 0.12 | 45 | 4.31 (2.11-8.26) | 6.15E-05 | 20 | 6.60 (2.98-14.13) | 3.03E-06 | 396 | 4.60 (2.39-8.09) | 1.25E-05 |
| A3301 | 9 | 0 | Inf (0.77-Inf) | 0.07 | 39 | 3.40 (1.43-7.23) | 3.20E-03 | 32 | 2.80 (1.16-6.09) | 0.01 | 255 | 4.89 (2.19-9.56) | 1.63E-04 |
| A0301 | 26 | 15 | 0.63 (0.31-1.35) | 0.20 | 592 | 0.59 (0.38-0.90) | 0.01 | 380 | 0.63 (0.40-0.97) | 0.03 | 5497 | 0.60 (0.38-0.90) | 0.01 |
| A0101 | 71 | 17 | 1.81 (0.99-3.48) | 0.04 | 662 | 1.73 (1.29-2.31) | 2.67E-04 | 448 | 1.74 (1.28-2.33) | 3.21E-04 | 7411 | 1.39 (1.05-1.83) | 0.02 |
| A3201 | 3 | 4 | 0.28 (0.04-1.70) | 0.10 | 152 | 0.38 (0.06-3.83) | 0.01 | 105 | 0.37 (0.05-0.82) | 0.02 | 1323 | 0.30 (0.06-0.80) | 0.02 |
| A0201 | 64 | 24 | 1.03 (0.59-1.85) | 1.00 | 1085 | 0.80 (0.59-1.08) | 0.14 | 756 | 0.78 (0.57-1.04) | 0.09 | 10680 | 0.75 (0.56-1.00) | 0.05 |
| A2302 | 10 | 1 | 3.95 (0.55-173.12) | 0.30 | 48 | 3.07 (1.37-6.24) | 3.65E-03 | 37 | 2.70 (1.18-5.61) | 9.43E-03 | 750 | 1.83 (0.86-3.43) | 0.08 |
| A2601 | 8 | 3 | 1.03 (0.24-6.13) | 1.00 | 115 | 1.00 (0.42-2.07) | 1.00 | 91 | 0.85 (0.35-1.78) | 0.86 | 834 | 1.30 (0.55-2.62) | 0.41 |
| A2501 | 3 | 2 | 0.57 (0.06-6.96) | 0.62 | 101 | 0.42 (0.08-1.28) | 0.16 | 47 | 0.62 (0.12-1.94) | 0.62 | 673 | 0.60 (0.12-1.77) | 0.50 |
| A2402 | 23 | 11 | 0.79 (0.35-1.86) | 0.55 | 356 | 0.92 (0.57-1.44) | 0.83 | 249 | 0.89 (0.55-1.40) | 0.74 | 2801 | 1.12 (0.69-1.72) | 0.57 |
| A3101 | 9 | 2 | 1.75 (0.35-16.85) | 0.73 | 115 | 1.13 (0.50-2.26) | 0.71 | 75 | 1.18 (0.51-2.39) | 0.57 | 1015 | 1.20 (0.54-2.33) | 0.58 |
| A1101 | 14 | 10 | 0.52 (0.21-1.34) | 0.16 | 255 | 0.78 (0.41-1.36) | 0.44 | 177 | 0.76 (0.40-1.33) | 0.44 | 2278 | 0.82 (0.44-1.40) | 0.61 |
| A2301 | 6 | 2 | 1.16 (0.20-11.91) | 1.00 | 94 | 0.92 (0.33-2.10) | 1.00 | 61 | 0.96 (0.34-2.24) | 1.00 | 672 | 1.21 (0.44-2.68) | 0.65 |
| A6801 | 9 | 8 | 0.42 (0.14-1.27) | 0.09 | 128 | 1.01 (0.45-2.01) | 0.86 | 100 | 0.87 (0.38-1.76) | 0.87 | 1142 | 1.07 (0.48-2.06) | 0.86 |
| A19 all (29,30,31,32,33) | 44 | 8 | 2.07 (0.92-4.64) | 0.08 | 399 | 1.49 (1.02-2.18) | 0.04 | 269 | 1.58 (1.07-2.34) | 0.02 | 3739 | 1.51 (1.04-2.18) | 0.03 |

Figure 1

| Second HLA-A Allele | UParis (A29 EUR Carriers) | | | | GHS cohort #1 (A29 EUR) | | | GHS cohort #2 (A29 EUR) | | | UKB* (A29 EUR) | | |
|---|---|---|---|---|---|---|---|---|---|---|---|---|---|
| | Cases n=286 | Ctrls n=108 | OR (LCI-UCI) | p-val | Carriers n=4014 | OR (LCI-UCI) | p-val | Carriers n=2829 | OR (LCI-UCI) | p-val | Carriers n=38,543 | OR (LCI-UCI) | p-val |
| A19 co-susceptible (29,30,31,33) | 41 | 4 | 4.05 (1.40-11.77) | 0.01 | 247 | 2.21 (1.47-3.33) | 1.55E-04 | 164 | 2.49 (1.63-3.81) | 2.34E-05 | 2416 | 2.24 (1.52-3.30) | 4.57E-05 |
| A3002 | 13 | 1 | 4.32 (0.55-33.79) | 0.16 | 45 | 2.78 (1.31-5.88) | 7.66E-03 | 20 | 4.26 (1.83-9.92) | 7.68E-04 | 396 | 4.01 (2.05-7.84) | 4.99E-05 |
| A3301 | 9 | 0 | 6204540.00 (0.00-inf) | 0.98 | 39 | 3.12 (1.29-7.58) | 0.01 | 32 | 2.69 (1.15-6.28) | 0.02 | 255 | 2.00 (0.80-5.01) | 0.14 |
| A0301 | 26 | 15 | 0.71 (0.35-1.45) | 0.35 | 592 | 0.69 (0.45-1.08) | 0.11 | 380 | 0.72 (0.46-1.14) | 0.16 | 5497 | 0.65 (0.43-1.01) | 0.05 |
| A0101 | 71 | 17 | 1.84 (1.01-3.35) | 0.05 | 662 | 1.57 (1.15-2.16) | 0.00 | 448 | 1.59 (1.15-2.19) | 0.01 | 7411 | 1.82 (1.35-2.45) | 0.00 |
| A3201 | 3 | 4 | 0.22 (0.05-1.04) | 0.05 | 152 | 0.30 (0.09-0.97) | 4.39E-02 | 105 | 0.22 (0.08-0.63) | 2.52E-02 | 1323 | 0.28 (0.08-0.90) | 3.33E-02 |
| A0201 | 64 | 24 | 0.97 (0.56-1.68) | 0.92 | 1085 | 0.87 (0.64-1.20) | 0.41 | 756 | 0.87 (0.63-1.20) | 0.41 | 10680 | 0.82 (0.61-1.11) | 0.20 |
| A2902 | 10 | 1 | 3.26 (0.40-26.32) | 0.27 | 48 | 1.63 (0.80-4.28) | 0.15 | 37 | 1.94 (0.84-4.46) | 0.12 | 750 | 2.10 (1.03-4.23) | 0.04 |
| A2601 | 8 | 3 | 1.09 (0.28-4.26) | 0.90 | 115 | 0.87 (0.39-1.91) | 0.72 | 91 | 0.91 (0.40-2.09) | 0.82 | 834 | 0.73 (0.33-1.61) | 0.44 |
| A2501 | 3 | 2 | 0.55 (0.08-3.61) | 0.54 | 101 | 0.57 (0.16-2.01) | 0.38 | 47 | 0.69 (0.18-2.62) | 0.59 | 673 | 0.66 (0.20-2.15) | 0.49 |
| A2402 | 23 | 11 | 0.85 (0.39-1.85) | 0.67 | 356 | 0.99 (0.61-1.61) | 0.97 | 249 | 1.06 (0.65-1.74) | 0.81 | 2801 | 1.00 (0.63-1.59) | 0.99 |
| A3101 | 9 | 2 | 1.75 (0.37-8.33) | 0.48 | 115 | 1.42 (0.68-2.97) | 0.35 | 75 | 1.57 (0.72-3.41) | 0.25 | 1015 | 1.24 (0.58-2.64) | 0.57 |
| A1101 | 14 | 10 | 0.55 (0.23-1.34) | 0.19 | 255 | 0.81 (0.45-1.48) | 0.50 | 177 | 0.83 (0.45-1.53) | 0.54 | 2278 | 0.82 (0.46-1.45) | 0.49 |
| A2301 | 6 | 2 | 1.06 (0.21-5.47) | 0.94 | 94 | 0.85 (0.34-2.17) | 0.74 | 61 | 0.73 (0.28-1.95) | 0.53 | 672 | 0.85 (0.35-2.10) | 0.73 |
| A6801 | 9 | 8 | 0.42 (0.16-1.15) | 0.09 | 128 | 0.95 (0.45-2.04) | 0.90 | 100 | 0.76 (0.35-1.67) | 0.50 | 1142 | 1.43 (0.70-2.91) | 0.33 |
| A19 all (29,30,31,32,33) | 44 | 8 | 2.07 (0.92-4.64) | 0.08 | 399 | 1.49 (1.02-2.18) | 0.04 | 269 | 1.58 (1.07-2.34) | 0.02 | 3739 | 1.51 (1.04-2.18) | 0.03 |

Figure 3

| Gene | Variant | Variant type | Study | OR (LCI-UCI) | p-value | Hom OR | Case MAF | Control MAF | Meta OR (LCI-UCI) | Meta p-value |
|---|---|---|---|---|---|---|---|---|---|---|
| ERAP2-LNPEP | rs10044354 5:96984791:C:T | Intronic | Kuiper et al. | 2.3 (1.69-3.61) | 1.21E-06 | | 0.63 | 0.42 | 1.95 (1.55-2.44) | 6.20E-09 |
| | | | UParis | 1.55 (1.13-2.11) | 5.80E-03 | 2.6 (1.3-5.15) | 0.52 | 0.41 | | |

Figure 4

| Gene | Variant | Variant type | Study | OR (LCI-UCI) | p-value | Hom OR | Case MAF | Control MAF | Meta OR (LCI-UCI) | Meta p-value |
|---|---|---|---|---|---|---|---|---|---|---|
| ERAP2 | rs2248374 5:96900192:A:G | Splice region | Kuiper et al. | 0.44 (0.31-0.63) | 6.60E-06 | | 0.33 | 0.53 | 0.56 (0.45-0.70) | 2.39E-07 |
| | | | UParis | 0.68 (0.5-0.92) | 1.40E-02 | 0.45 (0.23-0.87) | 0.43 | 0.53 | | |

Figure 5

| Aw19 | ERAP2-rs10044354 | case_n | contr_n | case_F | controlF | OR | OR CI_low | OR CI_high | P |
|---|---|---|---|---|---|---|---|---|---|
| A29/- | CC | 46 | 1296 | 0.167 | 0.319 | 1.000 | NA | NA | NA |
| A29/- | CT | 132 | 1842 | 0.478 | 0.453 | 2.019 | 1.421 | 2.911 | 3.95E-05 |
| A29/- | TT | 56 | 681 | 0.203 | 0.167 | 2.316 | 1.522 | 3.539 | 4.51E-05 |
| A29/Aw19 | CC | 13 | 94 | 0.047 | 0.023 | 3.891 | 1.861 | 7.644 | 2.13E-04 |
| A29/Aw19 | CT | 17 | 119 | 0.062 | 0.029 | 4.019 | 2.092 | 7.413 | 2.32E-05 |
| A29/Aw19 | TT | 12 | 34 | 0.043 | 0.008 | 9.902 | 4.378 | 21.197 | 1.16E-07 |

Figure 7

| Allele\position | 9 | 17 | 56 | 62 | 63 | 70 | 73 | 76 | 77 | 79 | 80 | 81 | 82 | 83 | 97 | 105 | 109 | 114 | 116 | 152 |
|---|---|---|---|---|---|---|---|---|---|---|---|---|---|---|---|---|---|---|---|---|
| A*01:01:01:01 | F | R | G | Q | E | H | T | A | N | G | T | L | R | G | I | P | F | R | D | A |
| A*29:02:01:01 | T | S | . | L | Q | Q | . | E | . | . | . | . | . | . | M | S | . | E | H | V |
| A*30:02:01:01 | S | . | R | . | . | . | . | V | D | . | . | . | . | . | . | S | . | Q | . | R |
| A*31:01:02:01 | T | . | R | . | . | . | I | E | S | . | . | . | . | . | M | S | . | Q | . | V |
| A*32:01:01:01 | . | . | . | R | N | . | I | V | D | R | . | A | L | R | M | . | . | Q | . | V |
| A*33:01:01:01 | T | . | . | . | . | . | . | V | D | . | . | . | . | . | M | S | L | Q | . | V |
| A*74:01:01:01 | . | . | . | . | . | . | . | V | D | . | . | . | L | . | M | . | L | Q | . | V |

Figure 8

MATERIALS AND METHODS OF TREATING MHC-I-OPATHY RISK HAPLOTYPES

REFERENCE TO SEQUENCE LISTING

This application includes a Sequence Listing filed electronically as a text file named 18923810701SEQ, created on Apr. 6, 2022, with a size of 1027 kilobytes. The Sequence Listing is incorporated herein by reference.

FIELD

The present disclosure is directed, in part, to methods of treating subjects having an immune disorder by administering to the subject a therapeutically effective amount of an Endoplasmic Reticulum Aminopeptidase 2 (ERAP2) inhibitor in combination with an HLA-A29 or HLA-B27 inhibitory nucleic acid molecule.

BACKGROUND

The cellular immune response in humans relies at least partly on the presentation of small peptides that are 8 to 10 amino acids long, which are bound proteins of the major histocompatibility complex (MHC) (i.e., class I MHC molecules). These small peptides are derived from the proteolytic degradation of proteins (foreign antigens and self-antigens). One source of these antigens come from infected or malignantly transformed cells that express particular protein molecules that, upon degradation, yield distinct antigenic peptides that are presented on the cell surface complexed with MHC class I molecules (MHCI). Cytotoxic T cells can recognize these complexes of MHC molecules with degraded protein antigens and induce apoptotic cell death. Aberrant generation of antigenic peptides can lead to immune system evasion or to autoimmune reactions.

Although most antigenic peptides are initially produced by the proteasome, many of them are larger than the final antigenic epitope and contain one or more additional amino acids at their N-termini. These antigenic peptide precursors are transported into the endoplasmic reticulum (ER), where they are further degraded by at least two different aminopeptidases, ERAP1 and ERAP2, to generate the mature antigenic peptides for complexing with MHC class I molecules. Thus, the activity of ERAP1 and ERAP2 can directly affect the presentation of antigenic peptides complexed with particular MHC molecules in a beneficial or adverse manner, thus altering the immune response. Accordingly, there continues to be a need for identifying subjects that have particular MHC-I-opathies related to ERAP2 activity and treatment of the same.

Birdshot Chorioretinopathy (BSCR) is a rare autoimmune uveitis predominately affecting individuals over the age of 50 of European descent and treated with immunomodulatory therapies. The disease presents with vitritis and gradual decline in vision due to choroidal and retinal inflammatory lesions and atrophy. T cells have been identified in the retinal and choroidal tissues as well as the vitreous of affected BSCR eyes.

SUMMARY

The present disclosure provides methods of treating a subject having an immune disorder, the methods comprising administering to the subject an ERAP2 inhibitor and: i) an HLA-A29 inhibitor and/or ii) an HLA-B27 inhibitor.

The present disclosure provides methods of treating a subject having an MHC-I-opathy, the methods comprising: performing or having performed an assay on a biological sample from the subject to determine whether the subject comprises: i) an HLA-A29 allele and/or an HLA-B27 allele; and ii) a functional ERAP2 protein or a nucleic acid molecule encoding a functional ERAP2 protein; and administering to the subject a therapeutically effective amount of an ERAP2 inhibitor and an HLA-A29 inhibitor to the subject having the functional ERAP2 protein or the nucleic acid molecule encoding a functional ERAP2 protein, and having the HLA-A29 allele; or administering to the subject a therapeutically effective amount of an ERAP2 inhibitor and an HLA-B27 inhibitor to the subject having the functional ERAP2 protein or the nucleic acid molecule encoding a functional ERAP2 protein, and having the HLA-B27 allele; wherein the presence of both: i) the HLA-A29 allele and/or the HLA-B27 allele, and ii) the functional ERAP2 protein or the nucleic acid molecule encoding a functional ERAP2 protein, indicates that the subject is a candidate for treating the MHC-I-opathy by inhibiting ERAP2.

The present disclosure provides combinations of an ERAP2 inhibitor and an HLA-A29 inhibitor for use in the treatment of an immune disorder.

The present disclosure provides combinations of an ERAP2 inhibitor and an HLA-B27 inhibitor for use in the treatment of an immune disorder.

BRIEF DESCRIPTION OF THE DRAWINGS

FIG. 1 shows a table of HLA-A 2nd allele frequencies in the French cohort compared to UKB and GHS EUR A29 carriers. Alleles belonging to the Aw19 broad antigen group that increase risk are A29 (eighth row), A30 (second row), A31 (twelfth row) and A33 (third row) and A32 exhibits protection (third row). A Fisher's exact test combining all Aw19 risk alleles presents the strongest enrichment in all comparisons (first row). Only alleles that have three or more case carriers are presented. Table is sorted by p-values when comparing case frequencies against A29 controls in UKB.

FIG. 3 shows a table of HLA-A 2nd allele frequencies in the French cohort compared to UKB and GHS EUR A29 carriers. Alleles belonging to the Aw19 broad antigen group that increase risk are A29 (eighth row), A30 (second row), A31 (twelfth row) and A33 (third row) and A32 exhibits protection (sixth row). A logistic regression test with covariates included for sex and six principal components, calculated based on genetic array data for each analytic set. Results are presented for all HLA-A alleles that have three or more case carriers. Alleles are sorted as in FIG. 1. * Three principal components.

FIG. 4 shows a table of top SNPs in ERAP2 regions. Variants in ERAP2 are genome-wide significant when analyzed together with previous results (125 cases and 670 controls (Kuiper 2014). Rs10044354 is the top association in the ERAP1-ERAP2 locus in the previous GWAS of Dutch and Spanish cohorts, while rs27432 is the top association in the region in the current French cohort. The LD between the two loci is also presented. *The reference A-allele is the minor allele, risk is the G-allele.

FIG. 5 shows ERAP2 splice region variant is protective for BSCR. The common ERAP2 splice region variant rs2248374 that disrupts ERAP2 expression is protective in the current BSCR cohort and the previous Spanish and Dutch cohorts.

FIG. 7 shows a table of the combined risk of ERAP2 and Aw19. Utilizing 286 Birdshot cases and 4,014 controls from GHS cohort #1 to calculate additive risk while combining risk factors in ERAP2 and Aw19. An additive genotype model of ERAP2 risk signal tagged by rs10044354 and single (A29/-) or double (A29/Aw19) Aw19 copies relative to lowest risk combination of rs10044354-CC and one copy of Aw19 allele (A29).

FIG. 8 shows differences between risk Aw19 alleles and A32. Sequence differences between risk Aw19 alleles (second, third, fourth, and sixth rows) and protective A32 allele (fifth row). A32 exhibits F at position 9 as is the reference A:01:01 allele, while risk alleles are either T or S at that position. The Bw4 epitope sequence is apparent at positions 79-83 or A32 only. The risk allele at position 17 is S; the risk alleles at position 62 are L or R; the risk alleles at position 63 are Q or N; the risk allele at position 70 is Q; the risk allele at position 73 is I; the risk allele at position 105 is S; the risk allele at position 116 is H; and the risk allele at position 152 is R.

DESCRIPTION OF EMBODIMENTS

Figure 2:
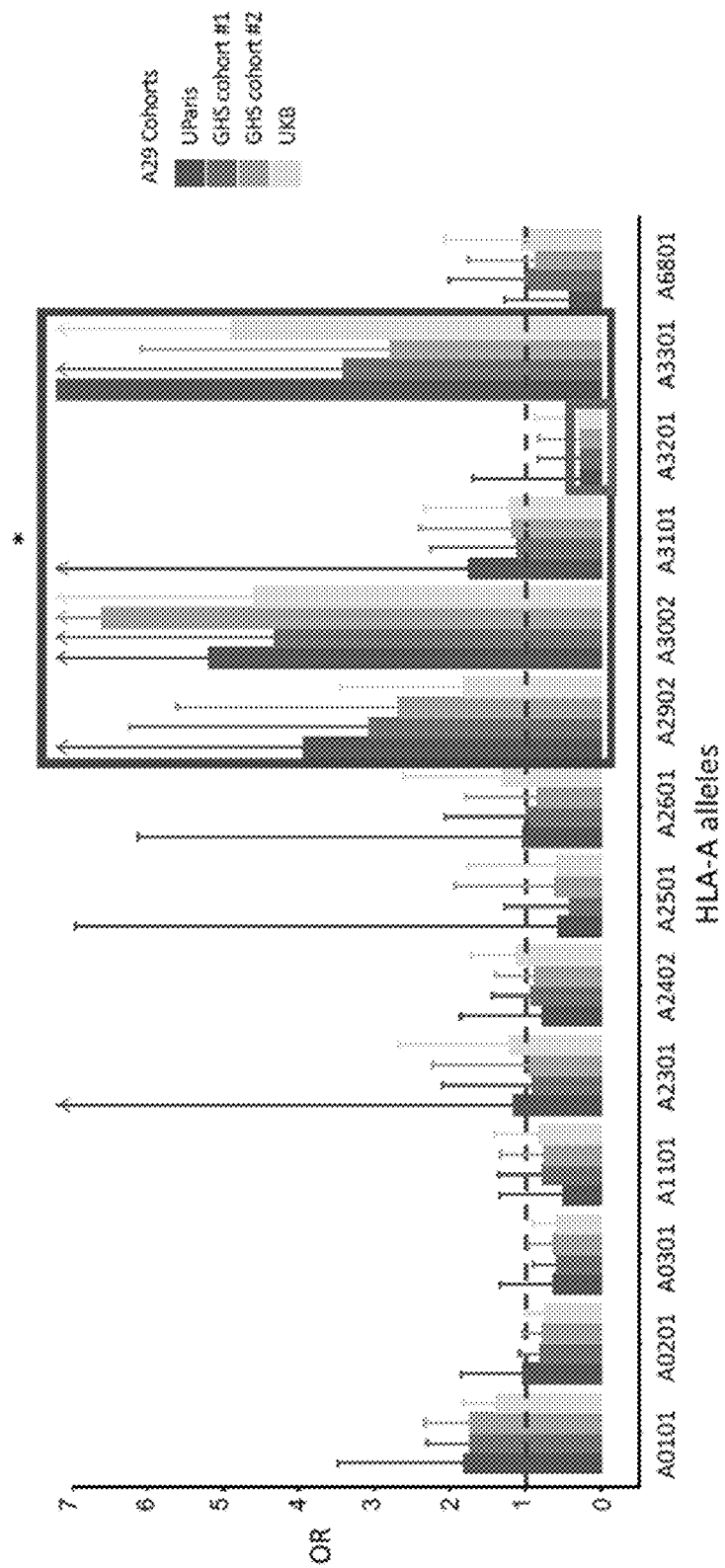
FIG. 2 shows Aw19 enrichment in Birdshot cases. Odds-ratio for BSCR, comparing frequencies of 14 HLA-A alleles that are present in three or more cases (>1%, x-axis) in 286 UParis cases compared with 108 UParis controls, GHS control cohort #1 (n=4,014), GHS control cohort #2 (n=2,829) and UKB controls 38,543). Aw19 alleles show the highest ORs (large box) that replicates with large A29 control cohorts, with the exception of A32 that is depleted in cases (small box). * $p<0.01$

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates (such as, for example, apes and monkeys). In some embodiments, the subject is a human. In some embodiments, the subject is a patient under the care of a physician.

The present disclosure provides methods of treating a subject having an immune disorder, the methods comprising administering to the subject an ERAP2 inhibitor. In some embodiments, the immune disorder is an MHC-I-opathy. In some embodiments, the immune disorder is an MHC-II-opathy. In some embodiments, the MHC-I-opathy is Birdshot Chorioretinopathy (BSCR), Ankylosing Spondylitis (AS), psoriasis in combination with uveitis, or Juvenile Idiopathic Arthritis (JIA). In some embodiments, the MHC-I-opathy is BSCR. In some embodiments, the MHC-I-opathy is AS. In some embodiments, the MHC-I-opathy is psoriasis in combination with uveitis. In some embodiments, the MHC-I-opathy is JIA.

In some embodiments, the MHC-I-opathy is BSCR. In some embodiments, the method further comprises detecting the presence or absence of an HLA-Aw19 allele in a biological sample obtained from the subject. In some embodiments, the subject is HLA-Aw19$^+$. In some embodiments, the subject is or is suspected of being HLA-A29$^+$, HLA-A30$^+$, HLA-A31$^+$, or HLA-A33$^+$, or any combination thereof. In some embodiments, the method further comprises determining whether the subject has one or two copies of an HLA-Aw19 allele. In some embodiments, the subject has a single copy of HLA-Aw19. In some embodiments, the subject has two copies of HLA-Aw19. In some embodiments, the subject is HLA-A29$^+$/HLA-A30$^+$. In some embodiments, the subject is HLA-A29$^+$/HLA-A31$^+$. In some embodiments, the subject is HLA-A29$^+$/HLA-A33$^+$.

In some embodiments, the subject having BSCR is not HLA-A29$^+$.

In some embodiments, the subject having BSCR has a copy of at least any two of HLA-A29, HLA-A30, HLA-A31, or HLA-A33. In some embodiments, the subject having BSCR has a copy of at least any three of HLA-A29, HLA-A30, HLA-A31, or HLA-A33. In some embodiments, the subject having BSCR has a copy of all of HLA-A29, HLA-A30, HLA-A31, or HLA-A33.

In some embodiments, the subject having BSCR has one copy of each HLA-A29 and HLA-A30. In some embodiments, the subject having BSCR has one copy of each HLA-A29 and HLA-A31. In some embodiments, the subject having BSCR has one copy of each HLA-A29 and HLA-A33. In some embodiments, the subject having BSCR has one copy of each HLA-A30 and HLA-A31. In some embodiments, the subject having BSCR has one copy of each HLA-A30 and HLA-A33. In some embodiments, the subject having BSCR has one copy of each HLA-A31 and HLA-A33.

In some embodiments, the subject having BSCR has one copy of HLA-A29 and two copies of HLA-A30. In some embodiments, the subject having BSCR has one copy of HLA-A29 and two copies of HLA-A31. In some embodiments, the subject having BSCR has one copy of HLA-A29 and two copies of HLA-A33. In some embodiments, the subject having BSCR has one copy of HLA-A30 and two copies of HLA-A31. In some embodiments, the subject having BSCR has one copy of HLA-A30 and two copies HLA-A33. In some embodiments, the subject having BSCR has one copy of HLA-A31 and two copies of HLA-A33.

In some embodiments, the subject having BSCR has two copies of HLA-A29 and one copy of HLA-A30. In some embodiments, the subject having BSCR has two copies of HLA-A29 and one copy of HLA-A31. In some embodiments, the subject having BSCR has two copies of HLA-A29 and one copy of HLA-A33. In some embodiments, the subject having BSCR has two copies of HLA-A30 and one copy of HLA-A31. In some embodiments, the subject having BSCR has two copies of HLA-A30 and one copy of HLA-A33. In some embodiments, the subject having BSCR has two copies of HLA-A31 and one copy of HLA-A33.

In some embodiments, the subject having BSCR or suspected of having BSCR has two copies of HLA-A29 and two copies of HLA-A30. In some embodiments, the subject having BSCR or suspected of having BSCR has two copies of HLA-A29 and two copies of HLA-A31. In some embodiments, the subject having BSCR or suspected of having BSCR has two copies of HLA-A29 and two copies of HLA-A33. In some embodiments, the subject having BSCR or suspected of having BSCR has two copies of HLA-A30 and two copies of HLA-A31. In some embodiments, the subject having BSCR or suspected of having BSCR has two copies of HLA-A30 and two copies of HLA-A33. In some embodiments, the subject having BSCR or suspected of having BSCR has two copies of HLA-A31 and two copies of HLA-A33.

In some embodiments, the method further comprises administering to the subject an HLA-Aw19 inhibitor. In some embodiments, the HLA-Aw19 inhibitor comprises an antibody. In some embodiments, the antibody comprises an anti-HLA-A29 antibody. In some embodiments, the HLA-Aw19 inhibitor comprises a small molecule degrader or an inhibitory nucleic acid molecule. In some embodiments, the inhibitory nucleic acid molecule comprises an antisense nucleic acid molecule, a small interfering RNA (siRNA), or a short hairpin RNA (shRNA) that hybridizes to an HLA-Aw19. In some embodiments, the HLA-Aw19 is HLA-A29.

In some embodiments, the MHC-I-opathy is AS. In some embodiments, the method further comprises detecting the presence or absence of HLA-B27 or HLA-B40 in a biological sample obtained from the subject. In some embodiments, the subject is or is suspected of being HLA-B27$^+$. In some embodiments, the subject is or is suspected of being HLA-B40$^+$. In some embodiments, the method further comprises determining whether the subject has one or two copies of HLA-B27 or HLA-B40. In some embodiments, the subject has a single copy of HLA-B27 or HLA-B40. In some embodiments, the subject has two copies of HLA-B27 or HLA-B40. In some embodiments, the method further comprises administering to the subject an HLA-B27 inhibitor or an HLA-B40 inhibitor. In some embodiments, the HLA-B27 inhibitor or HLA-B40 inhibitor comprises an antibody. In some embodiments, the antibody comprises an anti-HLA-B27 antibody or an anti-HLA-B40 antibody. In some embodiments, the HLA-B27 inhibitor or HLA-B40 inhibitor comprises a small molecule degrader or an inhibitory nucleic acid molecule. In some embodiments, the inhibitory nucleic acid molecule comprises an antisense nucleic acid molecule, an siRNA, or an shRNA that hybridizes to an HLA-B27 or an HLA-B40.

In some embodiments, the MHC-I-opathy is psoriasis in combination with uveitis. In some embodiments, the uveitis is anterior uveitis. In some embodiments, the method further comprises detecting the presence or absence of HLA-B27 in a biological sample obtained from the subject. In some embodiments, the subject is or is suspected of being HLA-B27$^+$. In some embodiments, the method further comprises determining whether the subject has one or two copies of HLA-B27. In some embodiments, the subject has a single copy of HLA-B27. In some embodiments, the subject has two copies of HLA-B27. In some embodiments, the method further comprises administering to the subject an HLA-B27 inhibitor. In some embodiments, the HLA-B27 inhibitor comprises an antibody. In some embodiments, the antibody comprises an anti-HLA-B27 antibody. In some embodiments, the HLA-B27 inhibitor comprises a small molecule degrader or an inhibitory nucleic acid molecule. In some embodiments, the inhibitory nucleic acid molecule comprises an antisense nucleic acid molecule, an siRNA, or an shRNA that hybridizes to an HLA-B27.

In some embodiments, the MHC-I-opathy is JIA. In some embodiments, the method further comprises detecting the presence or absence of HLA-B27 and/or DRB1 in a biological sample obtained from the subject. In some embodiments, the subject is or is suspected of being HLA-B27$^+$ and/or DRB1$^+$. In some embodiments, the method further comprises determining whether the subject has one or two copies of HLA-B27 and/or DRB1. In some embodiments, the subject has a single copy of HLA-B27 and/or DRB1. In some embodiments, the subject has two copies of HLA-B27 and/or DRB1. In some embodiments, the method further comprises administering to the subject an HLA-B27 inhibitor and/or a DRB1 inhibitor. In some embodiments, the HLA-B27 inhibitor and/or DRB1 inhibitor comprises an antibody. In some embodiments, the antibody comprises an anti-HLA-B27 antibody or an anti-DRB1 antibody. In some embodiments, the HLA-B27 inhibitor and/or DRB1 inhibitor comprises a small molecule degrader or an inhibitory nucleic acid molecule. In some embodiments, the inhibitory nucleic acid molecule comprises an antisense nucleic acid molecule, an siRNA, or an shRNA that hybridizes to an HLA-B27 and/or an DRB1.

In some embodiments, the ERAP2 inhibitor comprises a small molecule degrader, a proteoloysis-targeting chimera, an immunomodulatory drug, or an inhibitory nucleic acid molecule. In some embodiments, the inhibitory nucleic acid molecule comprises an antisense nucleic acid molecule, an siRNA, or an shRNA that hybridizes to ERAP2 mRNA. In some embodiments, the inhibitory nucleic acid molecule comprises an antisense nucleic acid molecule that hybridizes to ERAP2 mRNA. In some embodiments, the inhibitory nucleic acid molecule comprises an siRNA that hybridizes to ERAP2 mRNA. In some embodiments, the inhibitory nucleic acid molecule comprises an shRNA that hybridizes to ERAP2 mRNA. In some embodiments, the ERAP2 inhibitor comprises an anti-ERAP2 antibody. In some embodiments, the ERAP2 inhibitor comprises a pseudopeptide. In some embodiments, the pseudopeptide is a phosphinic pseudopeptide. In some embodiments, the phosphinic pseudopeptide is DG002 or DG013 (see, for example, Zervoudi et al., Proc. Natl. Acad. Sci. USA, 2013, 110, 19890-19895). In some embodiments, the phosphinic pseudopeptide is DG002. In some embodiments, the phosphinic pseudopeptide is DG013. In some embodiments, the ERAP2 inhibitor comprises a small molecule. In some embodiments, the ERAP2 inhibitor is compound 4, compound 15, compound 16, compound 5, or analogues of compound 5, which are drug-like carboxylic acids and bioisosters screened for enhanced selectivity for ERAP2 over ERAP1 (see, Medve et al., European Journal of Medicinal Chemistry, 2021, 211, 113053). In some embodiments, the ERAP2 inhibitor is a phosphonic or phosphinic acid compound with higher affinity for ERAP2 than ERAP1 (see, Weglarz-Tomczak et al., Bioorg. Med. Chem. Lett., 2016, 26, 4122-4126). Additional ERAP2 inhibitors are described in, for example, Georgiadis et al., Curr. Medic. Chem., 2019, 26, 2715-2729.

In any of the embodiments described herein, any of the inhibitors or other agents described herein can form a component of an antibody-drug-conjugate (ADC). For example, an ERAP2 inhibitor can be conjugated to an antibody, or antigen-binding fragment thereof. The inhibitor can comprise a small molecule degrader, a proteoloysis-targeting chimera, an immunomodulatory drug, or an inhibitory nucleic acid molecule.

The present disclosure also provides methods of treating a subject having an MHC-1-opathy. In some embodiments, the method comprises performing or having performed an assay on a biological sample from the subject to determine whether the subject comprises: i) an MHC-I-opathy-related HLA genotype; and ii) a functional ERAP2 protein or a nucleic acid molecule encoding a functional ERAP2 protein. In some embodiments, the method comprises administering to the subject a therapeutically effective amount of an ERAP2 inhibitor, wherein the subject comprises both an MHC-I-opathy-related HLA genotype and a functional ERAP2 protein or a nucleic acid molecule encoding a functional ERAP2 protein. The presence of both the MHC-I-opathy-related HLA genotype and the functional ERAP2 protein or a nucleic acid molecule encoding a functional ERAP2 protein indicates that the subject is a candidate for treating the MHC-I-opathy by inhibiting ERAP2.

In some embodiments, the MHC-I-opathy is BSCR and the MHC-I-opathy-related HLA genotype comprises an HLA-Aw19 allele. In some embodiments, the HLA-Aw19 allele comprises an HLA-A29 allele, an HLA-A30 allele, an HLA-A31 allele, or an HLA-A33 allele, or any combination thereof. In some embodiments, the subject has a single copy of the HLA-Aw19 allele. In some embodiments, the HLA-Aw19 allele comprises an HLA-A29 allele. In some embodiments, the HLA-Aw19 allele comprises an HLA-A30 allele. In some embodiments, the HLA-Aw19 allele comprises an HLA-A31 allele. In some embodiments, the HLA-Aw19 allele comprises an HLA-A33 allele. In some embodiments, the subject has two copies of the HLA-Aw19 allele. In some embodiments, the subject is or is suspected of being HLA-A29$^+$/HLA-A30$^+$. In some embodiments, the subject is or is suspected of being HLA-A29$^+$/HLA-A31$^+$. In some embodiments, the subject is or is suspected of being HLA-A29$^+$/HLA-A33$^+$.

In some embodiments, the subject having BSCR is not HLA-A29$^+$.

In some embodiments, the subject having BSCR has a copy of at least any two of HLA-A29, HLA-A30, HLA-A31, or HLA-A33. In some embodiments, the subject having BSCR has a copy of at least any three of HLA-A29, HLA-A30, HLA-A31, or HLA-A33. In some embodiments, the subject having BSCR has a copy of all of HLA-A29, HLA-A30, HLA-A31, or HLA-A33.

In some embodiments, the subject having BSCR has one copy of each HLA-A29 and HLA-A30. In some embodiments, the subject having BSCR has one copy of each HLA-A29 and HLA-A31. In some embodiments, the subject having BSCR has one copy of each HLA-A29 and HLA-A33. In some embodiments, the subject having BSCR has one copy of each HLA-A30 and HLA-A31. In some embodiments, the subject having BSCR has one copy of each HLA-A30 and HLA-A33. In some embodiments, the subject having BSCR has one copy of each HLA-A31 and HLA-A33.

In some embodiments, the subject having BSCR has one copy of HLA-A29 and two copies of HLA-A30. In some embodiments, the subject having BSCR has one copy of HLA-A29 and two copies of HLA-A31. In some embodiments, the subject having BSCR has one copy of HLA-A29 and two copies of HLA-A33. In some embodiments, the subject having BSCR has one copy of HLA-A30 and two copies of HLA-A31. In some embodiments, the subject having BSCR has one copy of HLA-A30 and two copies HLA-A33. In some embodiments, the subject having BSCR has one copy of HLA-A31 and two copies of HLA-A33.

In some embodiments, the subject having BSCR has two copies of HLA-A29 and one copy of HLA-A30. In some embodiments, the subject having BSCR has two copies of HLA-A29 and one copy of HLA-A31. In some embodiments, the subject having BSCR has two copies of HLA-A29 and one copy of HLA-A33. In some embodiments, the subject having BSCR has two copies of HLA-A30 and one copy of HLA-A31. In some embodiments, the subject having BSCR has two copies of HLA-A30 and one copy of HLA-A33. In some embodiments, the subject having BSCR has two copies of HLA-A31 and one copy of HLA-A33.

In some embodiments, the subject having BSCR or suspected of having BSCR has two copies of HLA-A29 and two copies of HLA-A30. In some embodiments, the subject having BSCR or suspected of having BSCR has two copies of HLA-A29 and two copies of HLA-A31. In some embodiments, the subject having BSCR or suspected of having BSCR has two copies of HLA-A29 and two copies of HLA-A33. In some embodiments, the subject having BSCR or suspected of having BSCR has two copies of HLA-A30 and two copies of HLA-A31. In some embodiments, the subject having BSCR or suspected of having BSCR has two copies of HLA-A30 and two copies of HLA-A33. In some embodiments, the subject having BSCR or suspected of having BSCR has two copies of HLA-A31 and two copies of HLA-A33.

In some embodiments, the method further comprises administering to the subject an HLA-Aw19 inhibitor. In some embodiments, the HLA-Aw19 inhibitor comprises an antibody. In some embodiments, the antibody comprises an anti-HLA-A29 antibody. In some embodiments, the HLA-Aw19 inhibitor comprises a small molecule degrader or an inhibitory nucleic acid molecule. In some embodiments, the inhibitory nucleic acid molecule comprises an antisense nucleic acid molecule, an siRNA, or an shRNA that hybridizes to an HLA-Aw19. In some embodiments, the HLA-Aw19 is HLA-A29.

In some embodiments, the MHC-I-opathy is AS and the MHC-I-opathy-related HLA genotype comprises an HLA-B27 allele or an HLA-B40 allele. In some embodiments, the subject has a single copy of HLA-B27 or HLA-B40. In some embodiments, the subject has two copies of HLA-B27 or HLA-B40. In some embodiments, the method further comprises administering to the subject an HLA-B27 inhibitor or an HLA-B40 inhibitor. In some embodiments, the HLA-B27 inhibitor or HLA-B40 inhibitor comprises an antibody. In some embodiments, the antibody comprises an anti-HLA- B27 antibody or an anti-HLA-B40 antibody. In some embodiments, the HLA-B27 inhibitor or HLA-B40 inhibitor comprises a small molecule degrader or an inhibitory nucleic acid molecule. In some embodiments, the inhibitory nucleic acid molecule comprises an antisense nucleic acid molecule, an siRNA, or an shRNA that hybridizes to an HLA-B27 or an HLA-B40.

In some embodiments, the MHC-I-opathy is psoriasis in combination with uveitis and the MHC-I-opathy-related HLA genotype comprises an HLA-B27 allele. In some embodiments, the uveitis is anterior uveitis. In some embodiments, the subject has a single copy of HLA-B27. In some embodiments, the subject has two copies of HLA-B27. In some embodiments, the method further comprises administering to the subject an HLA-B27 inhibitor. In some embodiments, the HLA-B27 inhibitor comprises an antibody. In some embodiments, the antibody comprises an anti-HLA-B27 antibody. In some embodiments, the HLA-B27 inhibitor comprises a small molecule degrader or an inhibitory nucleic acid molecule. In some embodiments, the inhibitory nucleic acid molecule comprises an antisense nucleic acid molecule, an siRNA, or an shRNA that hybridizes to an HLA-B27.

In some embodiments, the MHC-I-opathy is JIA and the MHC-I-opathy-related HLA genotype comprises an HLA-B27 and/or DRB1. In some embodiments, the subject has a single copy of HLA-B27 and/or DRB1. In some embodiments, the subject has two copies of HLA-B27 and/or. In some embodiments, the method further comprises administering to the subject an HLA-B27 inhibitor and/or a DRB1 inhibitor. In some embodiments, the HLA-B27 inhibitor and/or DRB1 inhibitor comprises an antibody. In some embodiments, the antibody comprises an anti-HLA-B27 antibody and/or a DRB1 antibody. In some embodiments, the HLA-B27 inhibitor and/or DRB1 inhibitor comprises a small molecule degrader or an inhibitory nucleic acid molecule. In some embodiments, the inhibitory nucleic acid molecule comprises an antisense nucleic acid molecule, an siRNA, or an shRNA that hybridizes to an HLA-B27 or DRB1.

In any of the embodiments described herein, the nucleic acid molecule comprises genomic DNA, mRNA, or cDNA obtained from mRNA. In some embodiments, the nucleic acid molecule comprises genomic DNA. In some embodiments, the nucleic acid molecule comprises mRNA. In some embodiments, the nucleic acid molecule comprises cDNA obtained from mRNA.

In any of the embodiments described herein, the ERAP2 inhibitor comprises a small molecule degrader, a proteoloysis-targeting chimera, an immunomodulatory drug, or an inhibitory nucleic acid molecule. In some embodiments, the inhibitory nucleic acid molecule comprises an antisense nucleic acid molecule, an siRNA, or an shRNA that hybridizes to ERAP2 mRNA. In some embodiments, the inhibitory nucleic acid molecule comprises an antisense nucleic acid molecule that hybridizes to ERAP2 mRNA. In some embodiments, the inhibitory nucleic acid molecule comprises an siRNA that hybridizes to ERAP2 mRNA. In some embodiments, the inhibitory nucleic acid molecule comprises an shRNA that hybridizes to ERAP2 mRNA. In some embodiments, the ERAP2 inhibitor comprises an anti-ERAP2 antibody. In some embodiments, the ERAP2 inhibitor comprises a pseudopeptide. In some embodiments, the pseudopeptide is a phosphinic pseudopeptide. In some embodiments, the phosphinic pseudopeptide is DG002 or DG013. In some embodiments, the ERAP2 inhibitor comprises a small molecule.

HLA-class-I antibodies can be generated by numerous methodologies with different degrees of antigen/allele specificity attained and are reported to be used for in vitro assays. HLA-B27 antibodies can be generated by numerous methodologies. In addition, three commercially available antibodies for HLA-B27 flow cytometric screening include the monoclonal mouse anti-human ABC-m3, FD705, and GS145.2 which have been shown to each have differing levels of cross-reactivity to other HLA-B antigens/alleles (Levering et al., Cytometry B Clin. Cytom., 2003, 54, 28-38).

In some embodiments, the assay for determining whether the subject comprises an MHC-I-opathy-related and/or MHC-II-opathy-related HLA genotype and a functional ERAP2 protein, or a nucleic acid molecule encoding a functional ERAP2 protein, is a genotyping assay or sequencing assay. In some embodiments, the nucleic acid molecule encoding a functional ERAP2 protein comprises genomic DNA, mRNA, or cDNA obtained from mRNA. By comparing the nucleotide or protein sequence of the ERAP2 protein in the sample from a subject to the wild type sequence for ERAP2 protein or nucleic acid molecule, or to published sequences of variant ERAP2 proteins or nucleic acid molecules having reduced or no activity, a determination can be made whether the subject comprises a functional ERAP2 protein, or a nucleic acid molecule encoding a functional ERAP2 protein. In addition, although an individual ERAP2 protein may have biological activity, the overall function of the ERAP2 protein may not be functional due to reduced levels of expression. Thus, as used herein, an ERAP2 protein can be determined not to be functional because the ERAP2 protein lacks or had reduced biological activity or because the expression level is reduced.

Determining whether a subject has an MHC-I-opathy-related and/or MHC-II-opathy-related HLA genotype and/or a functional ERAP2 protein, or a nucleic acid molecule encoding a functional ERAP2 protein, in a biological sample from a subject can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a biological sample obtained from the subject.

The biological sample can be derived from any cell, tissue, or biological fluid from the subject. The biological sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any particular nucleic acid molecule, preliminary processing designed to isolate or enrich the biological sample for the particular nucleic acid molecule can be employed. A variety of techniques may be used for this purpose. Various methods to detect the presence or level of an mRNA molecule or the presence of a particular genomic DNA locus can be used.

In some embodiments, the biological sample comprises a cell or cell lysate. Such methods can further comprise, for example, obtaining a biological sample from the subject comprising genomic nucleic acid molecules or mRNA molecules, and if mRNA, optionally reverse transcribing the mRNA into cDNA. In some embodiments, the method is an in vitro method. In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

Administration of any of the therapeutic agents described herein (including the ERAP2 inhibitor, and/or the HLA inhibitor) can be in a therapeutically effective amount to be determined by a health care professional. Administration of any of the therapeutic agents can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of any of the therapeutic agents can occur by any suitable route including, but not limited to, parenteral, intravenous, oral, subcutaneous, intra-arterial, intracranial, intrathecal, intraperitoneal, topical, intranasal, intra-articular, intravitreal, intracameral, subretinal, suprachoroidal, or intramuscular.

Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in an MHC-I-opathy and/or MHC-II-opathy, a decrease/reduction in the severity of an MHC-I-opathy and/or MHC-II-opathy (such as, for example, a reduction or inhibition of development of an MHC-I-opathy and/or MHC-II-opathy), a decrease/reduction in symptoms and MHC-I-opathy-related effects and/or MHC-II-opathy-related effects, delaying the onset of symptoms and MHC-I-opathy-related effects and/or MHC-II-opathy-related effects, reducing the severity of symptoms of MHC-I-opathy-related effects and/or MHC-II-opathy-related effects, reducing the severity of an acute episode, reducing the number of symptoms and MHC-I-opathy-related effects and/or MHC-II-opathy-related effects, reducing the latency of symptoms and MHC-I-opathy-related effects and/or MHC-II-opathy-related effects, an amelioration of symptoms and MHC-I-opathy-related effects and/or MHC-II-opathy-related effects, reducing secondary symptoms, reducing secondary infections, preventing relapse to an MHC-I-opathy and/or MHC-II-opathy, decreasing the number or frequency of relapse episodes, increasing latency between symptomatic episodes, increasing time to sustained progression, speeding recovery, or increasing efficacy of or decreasing resistance to alternative therapeutics, and/or an increased survival time of the subject, following administration of the agent or composition comprising the agent. A prophylactic effect may comprise a complete or partial avoidance/inhibition or a delay of an MHC-I-opathy and/or MHC-II-opathy development/progression (such as, for example, a complete or partial avoidance/inhibition or a delay), and an increased survival time of the affected subject, following administration of a therapeutic protocol. Treatment of an MHC-I-opathy and/or MHC-II-opathy encompasses the treatment of subjects already diagnosed as having any form of the MHC-I-opathy and/or MHC-II-opathy at any clinical stage or manifestation, the delay of the onset or evolution or aggravation or deterioration of the symptoms or signs of an MHC-I-opathy and/or MHC-II-opathy, and/or preventing and/or reducing the severity of an MHC-I-opathy and/or MHC-II-opathy.

In some embodiments, the ERAP2 antisense nucleic acid molecules comprise or consist of any of the nucleotide sequences represented by SEQ ID NOs: 1-858. In some embodiments, the ERAP2 siRNA molecules comprise or consist of any of the nucleotide sequences (sense and antisense strands presented one after the other) represented by SEQ ID NOs: 859-2748 (e.g., the sense strand is, for example, SEQ ID NO: 859 and the corresponding antisense strand is SEQ ID NO: 860; the sense strand is, for example, SEQ ID NO: 861 and the corresponding antisense strand is SEQ ID NO: 862; the sense strand is, for example, SEQ ID NO: 2747 and the corresponding antisense strand is SEQ ID NO: 2748; etc.).

In some embodiments, the HLA-A antisense nucleic acid molecules comprise or consist of any of the nucleotide sequences represented by SEQ ID NOs: 2749-2763. In some embodiments, the HLA-A siRNA molecules comprise or consist of any of the nucleotide sequences (sense and antisense strands presented one after the other) represented by SEQ ID NOs: 2764-2777 (e.g., the sense strand is, for example, SEQ ID NO: 2764 and the corresponding antisense strand is SEQ ID NO: 2765; the sense strand is, for example, SEQ ID NO: 2766 and the corresponding antisense strand is SEQ ID NO: 2767; the sense strand is, for example, SEQ ID NO: 2776 and the corresponding antisense strand is SEQ ID NO: 2777; etc.).

In some embodiments, the HLA-B antisense nucleic acid molecules comprise or consist of any of the nucleotide sequences represented by SEQ ID NO: 2778 and SEQ ID NO: 2779. In some embodiments, the HLA-B siRNA molecules comprise or consist of any of the nucleotide sequences (sense and antisense strands presented one after the other) represented by SEQ ID NOs: 2780-2783 (e.g., the sense strand is, for example, SEQ ID NO: 2780 and the corresponding antisense strand is SEQ ID NO: 2781; the sense strand is, for example, SEQ ID NO: 2783 and the corresponding antisense strand is SEQ ID NO: 2783).

In some embodiments, the HLA-C antisense nucleic acid molecules comprise or consist of any of the nucleotide sequences represented by SEQ ID NO: 2784 and SEQ ID NO: 2785. In some embodiments, the HLA-C siRNA molecules comprise or consist of any of the nucleotide sequences (sense and antisense strands presented one after the other) represented by SEQ ID NO: 2786 and SEQ ID NO: 2787.

In some embodiments, the B27 antisense nucleic acid molecules comprise or consist of any of the nucleotide sequences represented by SEQ ID NOs: 2788-3132. In some embodiments, the B27 siRNA molecules comprise or consist of any of the nucleotide sequences (sense and antisense strands presented one after the other) represented by SEQ ID NOs: 3133-3870 (e.g., the sense strand is, for example, SEQ ID NO: 3133 and the corresponding antisense strand is SEQ ID NO: 3134; the sense strand is, for example, SEQ ID NO: 3135 and the corresponding antisense strand is SEQ ID NO: 3136; the sense strand is, for example, SEQ ID NO: 3869 and the corresponding antisense strand is SEQ ID NO: 3870; etc.).

In some embodiments, the A29 antisense nucleic acid molecules comprise or consist of any of the nucleotide sequences represented by SEQ ID NOs: 3871-4145. In some embodiments, the A29 siRNA molecules comprise or consist of any of the nucleotide sequences (sense and antisense strands presented one after the other) represented by SEQ ID NOs: 4146-4755 (e.g., the sense strand is, for example, SEQ ID NO: 4146 and the corresponding antisense strand is SEQ ID NO: 4147; the sense strand is, for example, SEQ ID NO: 4148 and the corresponding antisense strand is SEQ ID NO: 4149; the sense strand is, for example, SEQ ID NO: 4754 and the corresponding antisense strand is SEQ ID NO: 4755; etc.).

The inhibitory nucleic acid molecules disclosed herein can comprise RNA, DNA, or both RNA and DNA. The inhibitory nucleic acid molecules can also be linked or fused to a heterologous nucleic acid sequence, such as in a vector, or a heterologous label. For example, the inhibitory nucleic acid molecules disclosed herein can be within a vector or as an exogenous donor sequence comprising the inhibitory nucleic acid molecule and a heterologous nucleic acid sequence. The inhibitory nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed inhibitory nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The inhibitory nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $-O[(CH_2)_nO]_mCH_3$, $-O(CH_2)_nOCH_3$, $-O(CH_2)_nNH_2$, $-O(CH_2)_nCH_3$, $-O(CH_2)_n-ONH_2$, and $-O(CH_2)_nON[(CH_2)_nCH_3)]_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

In some embodiments, the antisense nucleic acid molecules are gapmers, whereby the first one to seven nucleotides at the 5' and 3' ends each have 2'-methoxyethyl (2'-MOE) modifications. In some embodiments, the first five nucleotides at the 5' and 3' ends each have 2'-MOE modifications. In some embodiments, the first one to seven nucleotides at the 5' and 3' ends are RNA nucleotides. In some embodiments, the first five nucleotides at the 5' and 3' ends are RNA nucleotides. In some embodiments, each of the backbone linkages between the nucleotides is a phosphorothioate linkage.

In some embodiments, the siRNA molecules have termini modifications. In some embodiments, the 5' end of the antisense strand is phosphorylated. In some embodiments, 5'-phosphate analogs that cannot be hydrolyzed, such as 5'-(E)-vinyl-phosphonate are used.

In some embodiments, the siRNA molecules have backbone modifications. In some embodiments, the modified phosphodiester groups that link consecutive ribose nucleosides have been shown to enhance the stability and in vivo bioavailability of siRNAs The non-ester groups (—OH, =O) of the phosphodiester linkage can be replaced with sulfur, boron, or acetate to give phosphorothioate, boranophosphate, and phosphonoacetate linkages. In addition, substituting the phosphodiester group with a phosphotriester can facilitate cellular uptake of siRNAs and retention on serum components by eliminating their negative charge. In some embodiments, the siRNA molecules have sugar modifications. In some embodiments, the sugars are deprotonated (reaction catalyzed by exo- and endonucleases) whereby the 2'-hydroxyl can act as a nucleophile and attack the adjacent phosphorous in the phosphodiester bond. Such alternatives include 2'-O-methyl, 2'-O-methoxyethyl, and 2'-fluoro modifications.

In some embodiments, the siRNA molecules have base modifications. In some embodiments, the bases can be substituted with modified bases such as pseudouridine, 5'-methylcytidine, N6-methyladenosine, inosine, and N7-methylguanosine.

In some embodiments, the siRNA molecules are conjugated to lipids. Lipids can be conjugated to the 5' or 3' termini of siRNA to improve their in vivo bioavailability by allowing them to associate with serum lipoproteins. Representative lipids include, but are not limited to, cholesterol and vitamin E, and fatty acids, such as palmitate and tocopherol.

In some embodiments, a representative siRNA has the following formula:

Sense: mN*mN*/i2FN/mN/i2FN/mN/i2FN/mN/i2FN/mN/i2FN/mN/i2FN/mN/i2FN/mN/5 i2FN/*mN*/32FN/
Antisense: /52FN/*/i2FN/*mN/i2FN/mN/i2FN/mN/i2FN/mN/i2FN/mN/i2FN/mN/i2FN/mN/i2FN/mN*N*N wherein: "N" is the base; "2F" is a 2'-F modification; "m" is a 2'-O-methyl modification, "I" is an internal base; and "*" is a phosphorothioate backbone linkage.

The present disclosure also provides vectors comprising any one or more of the inhibitory nucleic acid molecules disclosed herein. In some embodiments, the vectors comprise any one or more of the inhibitory nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

The present disclosure also provides compositions comprising any one or more of the inhibitory nucleic acid molecules disclosed herein. In some embodiments, the composition is a pharmaceutical composition. In some embodiments, the compositions comprise a carrier and/or excipient. Examples of carriers include, but are not limited to, poly (lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

The present disclosure also provides methods of identifying a subject having an increased risk for developing an MHC-I-opathy and/or an MHC-II-opathy. The methods comprise performing or having performed an assay on a biological sample from the subject to determine whether the subject comprises: i) an MHC-I-opathy-related HLA genotype and/or an MHC-II-opathy-related HLA genotype; and ii) a functional ERAP2 protein or a nucleic acid molecule encoding a functional ERAP2 protein. When the subject has both the MHC-I-opathy-related HLA genotype and/or an MHC-II-opathy-related HLA genotype and the functional ERAP2 protein or the nucleic acid molecule encoding the functional ERAP2 protein, then the subject has an increased risk of developing the MHC-I-opathy and/or an MHC-II-opathy. When the subject lacks the MHC-I-opathy-related HLA genotype and/or an MHC-II-opathy-related HLA genotype, or lacks the functional ERAP2 protein or the nucleic acid molecule encoding the functional ERAP2 protein, or lacks both, then the subject has a decreased risk of developing the MHC-I-opathy and/or an MHC-II-opathy. In some embodiments, the method further comprises determining whether the subject has a single copy of the MHC-I-opathy-related HLA genotype and/or an MHC-II-opathy-related HLA genotype or two copies of the MHC-I-opathy-related HLA genotype and/or an MHC-II-opathy-related HLA genotype. When the subject comprises two copies of the MHC-I-opathy-related HLA genotype and/or an MHC-II-opathy-related HLA genotype, then the subject has an increased risk of developing the MHC-I-opathy and/or an MHC-II-opathy compared to comprising a single copy of the MHC-I-opathy-related HLA genotype and/or an MHC-II-opathy-related HLA genotype.

In some embodiments, the MHC-I-opathy is BSCR. In some embodiments, the subject is HLA-Aw19$^+$. In some embodiments, the subject is or is suspected of being HLA-A29$^+$, HLA-A30$^+$, HLA-A31$^+$, or HLA-A33$^+$, or any combination thereof. In some embodiments, the subject has a single copy of HLA-Aw19. In some embodiments, the subject has two copies of HLA-Aw19. In some embodiments, the subject is HLA-A29$^+$/HLA-A30$^+$. In some embodiments, the subject is HLA-A29$^+$/HLA-A31$^+$. In some embodiments, the subject is HLA-A29$^+$/HLA-A33$^+$.

In some embodiments, the subject having BSCR is not HLA-A29$^+$.

In some embodiments, the subject having BSCR has a copy of at least any two of HLA-A29, HLA-A30, HLA-A31, or HLA-A33. In some embodiments, the subject having BSCR has a copy of at least any three of HLA-A29, HLA-A30, HLA-A31, or HLA-A33. In some embodiments, the subject having BSCR has a copy of all of HLA-A29, HLA-A30, HLA-A31, or HLA-A33.

In some embodiments, the subject having BSCR has one copy of each HLA-A29 and HLA-A30. In some embodiments, the subject having BSCR has one copy of each HLA-A29 and HLA-A31. In some embodiments, the subject having BSCR has one copy of each HLA-A29 and HLA-A33. In some embodiments, the subject having BSCR has one copy of each HLA-A30 and HLA-A31. In some embodiments, the subject having BSCR has one copy of each HLA-A30 and HLA-A33. In some embodiments, the subject having BSCR has one copy of each HLA-A31 and HLA-A33.

In some embodiments, the subject having BSCR has one copy of HLA-A29 and two copies of HLA-A30. In some embodiments, the subject having BSCR has one copy of HLA-A29 and two copies of HLA-A31. In some embodiments, the subject having BSCR has one copy of HLA-A29 and two copies of HLA-A33. In some embodiments, the subject having BSCR has one copy of HLA-A30 and two copies of HLA-A31. In some embodiments, the subject having BSCR has one copy of HLA-A30 and two copies HLA-A33. In some embodiments, the subject having BSCR has one copy of HLA-A31 and two copies of HLA-A33.

In some embodiments, the subject having BSCR has two copies of HLA-A29 and one copy of HLA-A30. In some embodiments, the subject having BSCR has two copies of HLA-A29 and one copy of HLA-A31. In some embodiments, the subject having BSCR has two copies of HLA-A29 and one copy of HLA-A33. In some embodiments, the subject having BSCR has two copies of HLA-A30 and one copy of HLA-A31. In some embodiments, the subject having BSCR has two copies of HLA-A30 and one copy of HLA-A33. In some embodiments, the subject having BSCR has two copies of HLA-A31 and one copy of HLA-A33.

In some embodiments, the subject having BSCR or suspected of having BSCR has two copies of HLA-A29 and two copies of HLA-A30. In some embodiments, the subject having BSCR or suspected of having BSCR has two copies of HLA-A29 and two copies of HLA-A31. In some embodiments, the subject having BSCR or suspected of having BSCR has two copies of HLA-A29 and two copies of HLA-A33. In some embodiments, the subject having BSCR or suspected of having BSCR has two copies of HLA-A30 and two copies of HLA-A31. In some embodiments, the subject having BSCR or suspected of having BSCR has two copies of HLA-A30 and two copies of HLA-A33. In some embodiments, the subject having BSCR or suspected of having BSCR has two copies of HLA-A31 and two copies of HLA-A33.

In some embodiments, the method further comprises administering to the subject an HLA-Aw19 inhibitor. In some embodiments, the HLA-Aw19 inhibitor comprises an antibody. In some embodiments, the antibody comprises an anti-HLA-A29 antibody. In some embodiments, the HLA-Aw19 inhibitor comprises a small molecule degrader or an inhibitory nucleic acid molecule. In some embodiments, the inhibitory nucleic acid molecule comprises an antisense nucleic acid molecule, a small interfering RNA (siRNA), or a short hairpin RNA (shRNA) that hybridizes to an HLA-Aw19. In some embodiments, the HLA-Aw19 is HLA-A29.

In some embodiments, the MHC-I-opathy is AS. In some embodiments, the subject is or is suspected of being HLA-B27$^+$ or HLA-B40$^+$. In some embodiments, the subject has a single copy of HLA-B27 or HLA-B40. In some embodiments, the subject has two copies of HLA-B27 or HLA-B40. In some embodiments, the method further comprises administering to the subject an HLA-B27 inhibitor or an HLA-B40 inhibitor. In some embodiments, the HLA-B27 inhibitor or HLA-B40 inhibitor comprises an antibody. In some embodiments, the antibody comprises an anti-HLA-B27 antibody or an anti-HLA-B40 antibody. In some embodiments, the HLA-B27 inhibitor or HLA-B40 inhibitor comprises a small molecule degrader or an inhibitory nucleic acid molecule. In some embodiments, the inhibitory nucleic acid molecule comprises an antisense nucleic acid molecule, an siRNA, or an shRNA that hybridizes to an HLA-B27 or HLA-B40.

In some embodiments, the MHC-I-opathy is psoriasis in combination with uveitis. In some embodiments, the uveitis is anterior uveitis. In some embodiments, the subject is or is suspected of being HLA-B27$^+$. In some embodiments, the subject has a single copy of HLA-B27. In some embodiments, the subject has two copies of HLA-B27. In some embodiments, the method further comprises administering to the subject an HLA-B27 inhibitor. In some embodiments, the HLA-B27 inhibitor comprises an antibody. In some embodiments, the antibody comprises an anti-HLA-B27 antibody. In some embodiments, the HLA-B27 inhibitor comprises a small molecule degrader or an inhibitory nucleic acid molecule. In some embodiments, the inhibitory nucleic acid molecule comprises an antisense nucleic acid molecule, an siRNA, or an shRNA that hybridizes to an HLA-B27.

In some embodiments, the MHC-I-opathy is JIA. In some embodiments, the subject is or is suspected of being HLA-B27$^+$ and/or DRB1$^+$. In some embodiments, the subject has a single copy of HLA-B27 and/or DRB1. In some embodiments, the subject has two copies of HLA-B27 and/or DRB1. In some embodiments, the method further comprises administering to the subject an HLA-B27 inhibitor and/or a DRB1 inhibitor. In some embodiments, the HLA-B27 inhibitor and/or DRB1 inhibitor comprises an antibody. In some embodiments, the antibody comprises an anti-HLA-B27 antibody or an anti-DRB1 antibody. In some embodiments, the HLA-B27 inhibitor and/or DRB1 inhibitor comprises a small molecule degrader or an inhibitory nucleic acid molecule. In some embodiments, the inhibitory nucleic acid molecule comprises an antisense nucleic acid molecule, an siRNA, or an shRNA that hybridizes to an HLA-B27 and/or an DRB1.

In any of the embodiments described herein, the methods can further comprise administering to the subject having an increased risk of developing the MHC-I-opathy-related HLA genotype and/or an MHC-II-opathy an ERAP2 inhibitor. In some embodiments, the ERAP2 inhibitor comprises a small molecule degrader, a proteoloysis-targeting chimera, an immunomodulatory drug, or an inhibitory nucleic acid molecule. In some embodiments, the inhibitory nucleic acid molecule comprises an antisense nucleic acid molecule, an siRNA, or an shRNA that hybridizes to ERAP2 mRNA. In some embodiments, the inhibitory nucleic acid molecule comprises an antisense nucleic acid molecule that hybridizes to ERAP2 mRNA. In some embodiments, the inhibitory nucleic acid molecule comprises an siRNA that hybridizes to ERAP2 mRNA. In some embodiments, the inhibitory nucleic acid molecule comprises an shRNA that hybridizes to ERAP2 mRNA. In some embodiments, the ERAP2 inhibitor comprises an anti-ERAP2 antibody. In some embodiments, the ERAP2 inhibitor comprises a pseudopeptide. In some embodiments, the pseudopeptide is a phosphinic pseudopeptide. In some embodiments, the phosphinic pseudopeptide is DG002 or DG013. In some embodiments, the phosphinic pseudopeptide is DG002. In some embodiments, the phosphinic pseudopeptide is DG013. In some embodiments, the ERAP2 inhibitor comprises a small molecule.

In some embodiments, the assay for determining whether the subject comprises an MHC-I-opathy-related and/or MHC-II-opathy-related HLA genotype and a functional ERAP2 protein, or a nucleic acid molecule encoding a functional ERAP2 protein, is a genotyping assay or sequencing assay. In some embodiments, the nucleic acid molecule encoding a functional ERAP2 protein comprises genomic DNA, mRNA, or cDNA obtained from mRNA. By comparing the nucleotide or protein sequence of the ERAP2 protein in the sample from a subject to the wild type sequence for ERAP2 protein or nucleic acid molecule, or to published sequences of variant ERAP2 proteins or nucleic acid molecules having reduced or no activity, a determination can be made whether the subject comprises a functional ERAP2 protein, or a nucleic acid molecule encoding a functional ERAP2 protein. In addition, although an individual ERAP2 protein may have biological activity, the overall function of the ERAP2 protein may not be functional due to reduced levels of expression. Thus, as used herein, an ERAP2 protein can be determined not to be functional because the ERAP2 protein lacks or had reduced biological activity or because the expression level is reduced.

Determining whether a subject has an MHC-I-opathy-related and/or MHC-II-opathy-related HLA genotype and/or a functional ERAP2 protein, or a nucleic acid molecule encoding a functional ERAP2 protein, in a biological sample from a subject can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a biological sample obtained from the subject.

The biological sample can be derived from any cell, tissue, or biological fluid from the subject. The biological sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any particular nucleic acid molecule, preliminary processing designed to isolate or enrich the biological sample for the particular nucleic acid molecule can be employed. A variety of techniques may be used for this purpose. Various methods to detect the presence or level of an mRNA molecule or the presence of a particular genomic DNA locus can be used.

In some embodiments, the biological sample comprises a cell or cell lysate. Such methods can further comprise, for example, obtaining a biological sample from the subject comprising genomic nucleic acid molecules or mRNA molecules, and if mRNA, optionally reverse transcribing the mRNA into cDNA. In some embodiments, the method is an in vitro method. In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

Detecting the presence or absence of any particular HLA allele can be carried out by numerous techniques. Detection of HLA-A alleles on a 2-digit and 4-digit resolution can be carried out. For example, an assay that targets the HLA region in high resolution (all class-I and class-II genes) can be used. In some embodiments, the assay amplifies the full HLA gene (in this case HLA-A) from the 5'UTR to the 3'UTR and provides genetic variants across the full amplicon (the DNA that is the product of this amplification of the gene). A method can then be used to call the HLA-A alleles with high accuracy (e.g., PHLAT2; Bai et al., Methods Mol. Biol., 2018, 1802, 193-201). The output of PHLAT2 provides the HLA-A 4-digits allele data for each sample, which can be used for the analysis that identified other Aw19 alleles as enriched in Birdshot cases. In addition, commercial sources of HLA typing are available.

Detecting the presence or absence a functional ERAP2 protein, or a nucleic acid molecule encoding a functional ERAP2 protein, can be carried out by numerous techniques. For example, detection of presence or absence of ERAP2 protein and the relevant nucleotide sequence can be carried out as described in Andres et al., PLoS Genetics, 2010, 6, 1-13. For example, a subject having an ERAP2 intronic variant designated rs2248374-A has a functional ERAP2 protein, or a nucleic acid molecule encoding a functional ERAP2 protein, and has an increased risk of developing the MHC-I-opathy. A subject having an ERAP2 variant designated rs10044354, HapA has a functional ERAP2 protein, or a nucleic acid molecule encoding a functional ERAP2 protein, and has an increased risk of developing the MHC-I-opathy. A subject having an ERAP2 splice variant designated rs2248374-G does not have a functional ERAP2 protein, or a nucleic acid molecule encoding a functional ERAP2 protein, and has a decreased risk of developing the MHC-I-opathy.

Representative embodiments of the present disclosure include but are not limited to the following.

The present disclosure provides methods of treating a subject having an immune disorder, the methods comprising administering to the subject an ERAP2 inhibitor and: i) an HLA-A29 inhibitor and/or ii) an HLA-B27 inhibitor. In some embodiments, the immune disorder is an MHC-I-opathy.

The present disclosure also provides methods of treating a subject having an MHC-1-opathy, the methods comprising: performing or having performed an assay on a biological sample from the subject to determine whether the subject comprises: i) an HLA-A29 allele and/or an HLA-B27 allele; and ii) a functional ERAP2 protein or a nucleic acid molecule encoding a functional ERAP2 protein; and administering to the subject a therapeutically effective amount of an ERAP2 inhibitor and an HLA-A29 inhibitor to the subject having the functional ERAP2 protein or the nucleic acid molecule encoding a functional ERAP2 protein, and having the HLA-A29 allele; or administering to the subject a therapeutically effective amount of an ERAP2 inhibitor and an HLA-B27 inhibitor to the subject having the functional ERAP2 protein or the nucleic acid molecule encoding a functional ERAP2 protein, and having the HLA-B27 allele; wherein the presence of both: i) the HLA-A29 allele and/or the HLA-B27 allele, and ii) the functional ERAP2 protein or the nucleic acid molecule encoding a functional ERAP2 protein, indicates that the subject is a candidate for treating the MHC-I-opathy by inhibiting ERAP2.

The present disclosure also provides a combination of an ERAP2 inhibitor and an HLA-A29 inhibitor for use in the treatment of an immune disorder. The present disclosure also provides a combination of an ERAP2 inhibitor and an HLA-A29 inhibitor for use in the preparation of a medicament for treating an immune disorder. In some embodiments, the immune disorder is an MHC-I-opathy.

In some embodiments, the MHC-I-opathy is BSCR, and the method comprises administering the ERAP2 inhibitor and the HLA-A29 inhibitor to the subject. In some embodiments, the methods further comprise detecting the presence or absence of an HLA-A29 allele in a biological sample obtained from the subject. In some embodiments, the methods further comprise determining whether the subject has one or two copies of an HLA-A29 allele. In some embodiments, the HLA-29 inhibitor comprises an antibody. In some embodiments, the HLA-A29 inhibitor comprises a small molecule degrader or an inhibitory nucleic acid molecule. In some embodiments, the inhibitory nucleic acid molecule comprises an antisense nucleic acid molecule, an siRNA, or a short hairpin RNA that hybridizes to an HLA-A29. In some embodiments, the antisense nucleic acid molecule comprises a nucleotide sequence selected from the group consisting of SEQ ID NOs: 3871-4145. In some embodiments, the siRNA molecule comprises a sense strand and a corresponding antisense strand selected from the group consisting of SEQ ID NOs: 4146-4755.

In some embodiments, the MHC-I-opathy is AS, and the methods comprise administering the ERAP2 inhibitor and the HLA-B27 inhibitor to the subject. In some embodiments, the methods further comprise detecting the presence or absence of an HLA-B27 allele in a biological sample obtained from the subject. In some embodiments, the methods further comprise determining whether the subject has one or two copies of an HLA-B27 allele. In some embodiments, the HLA-B27 inhibitor comprises an antibody. In some embodiments, the HLA-B27 inhibitor comprises a small molecule degrader or an inhibitory nucleic acid molecule. In some embodiments, the inhibitory nucleic acid molecule comprises an antisense nucleic acid molecule, an siRNA, or a short hairpin RNA that hybridizes to an HLA-B27. In some embodiments, the antisense nucleic acid molecule comprises a nucleotide sequence selected from the group consisting of SEQ ID NOs: 2788-3132. In some embodiments, the siRNA molecule comprises a sense strand and a corresponding antisense strand selected from the group consisting of SEQ ID NOs: 3133-3870.

In some embodiments, the MHC-I-opathy is psoriasis and the subject also has uveitis, and the methods comprise administering the ERAP2 inhibitor and the HLA-B27 inhibitor to the subject. In some embodiments, the uveitis is anterior uveitis. In some embodiments, the methods further comprise detecting the presence or absence of an HLA-B27 allele in a biological sample obtained from the subject. In some embodiments, the methods further comprise determining whether the subject has one or two copies of an HLA-B27 allele. In some embodiments, the HLA-B27 inhibitor comprises an antibody. In some embodiments, the HLA-B27 inhibitor comprises a small molecule degrader or an inhibitory nucleic acid molecule. In some embodiments, the inhibitory nucleic acid molecule comprises an antisense nucleic acid molecule, an siRNA, or a short hairpin RNA that hybridizes to an HLA-B27. In some embodiments, the antisense nucleic acid molecule comprises a nucleotide sequence selected from the group consisting of SEQ ID NOs: 2788-3132. In some embodiments, the siRNA molecule comprises a sense strand and a corresponding antisense strand selected from the group consisting of SEQ ID NOs: 3133-3870.

In some embodiments, the MHC-I-opathy is JIA, and the methods comprise administering the ERAP2 inhibitor and the HLA-B27 inhibitor to the subject. In some embodiments, the methods further comprise detecting the presence or absence of an HLA-B27 allele in a biological sample obtained from the subject. In some embodiments, the methods further comprise determining whether the subject has one or two copies of an HLA-B27 allele. In some embodiments, the HLA-B27 inhibitor comprises an antibody. In some embodiments, the HLA-B27 inhibitor comprises a small molecule degrader or an inhibitory nucleic acid molecule. In some embodiments, the inhibitory nucleic acid molecule comprises an antisense nucleic acid molecule, an siRNA, or a short hairpin RNA that hybridizes to an HLA-B27. In some embodiments, the antisense nucleic acid molecule comprises a nucleotide sequence selected from the group consisting of SEQ ID NOs: 2788-3132. In some embodiments, the siRNA molecule comprises a sense strand and a corresponding antisense strand selected from the group consisting of SEQ ID NOs: 3133-3870.

In some embodiments, the ERAP2 inhibitor comprises a small molecule degrader or an inhibitory nucleic acid molecule. In some embodiments, the inhibitory nucleic acid molecule comprises an antisense nucleic acid molecule, an siRNA, or a short hairpin RNA that hybridizes to ERAP2 mRNA. In some embodiments, the antisense nucleic acid molecule comprises a nucleotide sequence selected from the group consisting of SEQ ID NOs: 1-858. In some embodiments, the siRNA molecule comprises a sense strand and a corresponding antisense strand selected from the group consisting of SEQ ID NOs: 859-2748. In some embodiments, the ERAP2 inhibitor comprises an anti-ERAP2 antibody. In some embodiments, the ERAP2 inhibitor comprises a pseudopeptide. In some embodiments, the pseudopeptide is a phosphinic pseudopeptide. In some embodiments, the phosphinic pseudopeptide is DG002 or DG013. In some embodiments, the ERAP2 inhibitor comprises a small molecule.

The present disclosure also provides pharmaceutical compositions comprising one or more ERAP2 inhibitors in combination with one or more HLA-A29 inhibitors. The present disclosure also provides pharmaceutical compositions comprising one or more ERAP2 inhibitors in combination with one or more HLA-B27 inhibitors. The present disclosure also provides pharmaceutical compositions comprising one or more ERAP2 inhibitors in combination with one or more HLA-A29 inhibitors and one or more HLA-B27 inhibitors.

In order that the subject matter disclosed herein may be more efficiently understood, examples are provided below. It should be understood that these examples are for illustrative purposes only and are not to be construed as limiting the claimed subject matter in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1: Methods

Study Subjects and Samples

The genomic DNA samples from 286 patients with BSCR and 108 unrelated healthy local French volunteers that exhibited HLA tissue typing common in the French population were included in this study. The patients were recruited at Hôpital Cochin, Paris, France. All patients met the criteria for diagnosis of BSCR as defined both by an international consensus conference held in 2002 and by the Standardization of Uveitis Nomenclature (SUN) Working Group. In brief, all patients had a posterior bilateral uveitis with multifocal cream-colored or yellow-orange, oval or round choroidal lesions ("birdshot spots"). Although the presence of the HLA-A29 allele was not a requirement for the diagnosis of BSCR according to the international criteria, all patients included in the current study carried the HLA-A29 allele. The control DNA samples were collected from volunteer donors recruited by the hematopoietic stem cell donor center of Rheims for France Greffe de Moelle Registry, and local control healthy individuals of the Registry. The DNA samples were isolated from peripheral blood samples using a standard salting out method or QIAamp Blood Kit (Qiagen, Chatsworth, CA, USA). Quality and quantity of DNA was determined by UV spectrophotometry and the concentration was adjusted to 100 ng/ml. Signed informed consent documentation was obtained from all participants, and all research adhered to the tenets set forth in the Declaration of Helsinki. All study-related data acquisitions were approved by the Paris Cochin institutional review board.

Genetic Data

A comprehensive approach was taken to both sequence the exomes and genotype all samples, to allow for identification of common and rare variants filtered based on high quality calls. DNA from participants was genotyped on the Illumina Global Screening Array (GSA) and imputed to the HRC reference panel. Prior to imputation, the variants that had a MAF>=0.1%, missingness <1% and HWE p-value >$10^{-15}$ were retained. Imputation using the HRC reference panel yielded 8,385,561 variants with imputation INFO>0.3 and MAF>0.5%.

Exome sequencing was performed to a mean depth of 31x, followed by variant calling and quality control as reported previously (Van Hout et al., Nature, 2020, 586, 749-756), resulting in 238,942 variants. When integrated, this produced an overall dataset with 8,459,907 variants: 65.5% common (MAF>5%), 34.5% low-frequency (0.5%<MAF<5%) and 0.01% rare (MAF<0.5%).

HLA Genotyping

HLA Class I genes (HLA-A, -B, and -C) were amplified in a multiplex PCR reaction with primers encompassing the full genomic loci for each target. The resulting amplicons were enzymatically fragmented to an average size of 250 base pairs and prepared for Illumina sequencing (New England Biolabs, Ipswich, MA). The libraries were sequenced on the Illumina HiSeq 2500 platform on a rapid run flow cell using paired-end 125 base pair reads with dual 10 base pair indexes. Upon completion of sequencing, raw data from each Illumina HiSeq run was gathered in local buffer storage and uploaded to the DNAnexus platform (Reid et al., BMC Bioinformatics, 2014, 15, 30) for automated analysis. The FASTQ-formatted reads were converted from the BCL files and assigned to samples identified by specific barcodes using the bcl2fastq conversion software (Illumina Inc., San Diego, CA). All the reads in sample-specific FASTQ files were subject to HLA typing analysis using an updated version of PHLAT program (Bai et al., BMC Genomics, 2014, 15, 325) with the reference sequences consisting of GRCh38 genomic sequences and HLA type reference sequences in the IPD-IMGT/HLA database v3.30.0 (Robinson et al., Hum. Immunol., 2016, 77, 233-237).

In addition, HLA allele imputation was performed following SNP2HLA (Jia et al., PLoS One, 2013, 8, e64683) with the T1DGC HLA allele reference panel (Rich et al., Ann. N.Y. Acad. Sci., 2006, 1079, 1-8). HRC-imputed genotypes in the extended Major Histocompatibility Complex (MHC) region (chr6:25-35 Mb) were filtered for high INFO score (>0.9) and certainty (maximum GP>0.8 for all genotyped), in order to increase overlap with the T1DGC reference panel, were re-phased along with chromosome 6 array genotypes using SHAPEIT4 (Delaneau et al., Nat. Commun., 2019, 10, 5436), and were imputed using Minimac4 (Das et al., Nat. Genet., 2016, 48, 1284-1287). HLA allele imputation quality was assessed by examining INFO score vs MAF, and imputed vs reference panel MAF.

Genetic Association Analyses

Association analyses in each study were performed using the genome-wide Firth logistic regression test implemented in SAIGE (Mbatchou et al., bioRxiv, 2020, 2020.2006.2019.162354, doi:10.1101/2020.06.19.162354; and Zhou et al., Nat. Genet., 2018, 50, 1335-1341). In this implementation, Firth's approach is applied when the p-value from standard logistic regression score test is below 0.05. The directly genotyped variants with a minor allele frequency (MAF)>1%, <10% missingness, Hardy-Weinberg equilibrium test P-value>$10^{-15}$ and linkage-disequilibrium (LD) pruning (1000 variant windows, 100 variant sliding windows and $r^2$<0.1) were included for GRM for SAIGE. The association model included as covariates sex and the first 10 ancestry-informative principal components (PCs) derived from the GRM dataset. Haplotype analyses were performed using PLINK 1.0 (Purcell et al., Am. J. Hum. Genet., 2007, 81, 559-575) --chap and --hap-assoc and --hap-logistic, and in R. High haplotype imputation and phasing quality was indicated by PLINK --hap-phase maximum likelihood haplotype genotypes' posterior probabilities all equal to one.

HLA-A Allele Association Analyses

Association of HLA-A alleles was performed as follows: for each sample, both HLA-A alleles were typed as described above. Following HLA allele typing, related samples were removed. For the remaining cohort of 282 cases and 106 controls, one HLA-A allele that is not A29 (the "second" allele) was obtained next. Samples carrying two copies of A29, were considered having A29 as the second allele. The cohort was then subjected to a Fisher's exact test, which tested the association of each allele that was identified in three or more BSCR cases, with the case-control status. To answer the question of whether the A19 allele group is also associated with the case-control status, the samples were combined, and tested together in two different ways: carrying all Aw19 alleles (A29, A30, A31, A32 and A33). Since A32 is biologically different than the other Aw19 alleles in its peptide binding domain, a group that is made of samples carrying all Aw19 alleles excluding A32 was also constructed and tested. The final odds-ratios and p-values are presented in the table in FIG. 1.

Example 2: HLA-Aw19 Broad Antigen Serotype Alleles and BSCR Risk

The HLA-A29-controlled cohort allowed for examination of the HLA region while controlling for the strong association of HLA-A29 with BSCR, and therefore to detect possible additional association signals in the HLA region.

First, it was asked whether rare variants on the HLA-A29 background were enriched in BSCR cases. No significant enrichments of rare single or aggregated variants were identified either within or outside the MHC region.

Second, the question was whether other HLA-A alleles in addition to the HLA-A29 allele increased BSCR risk. An assay to type HLA-A alleles in this cohort (see Methods) was constructed, and tested the second HLA-A allele (other than the known first HLA-A29) was tested for association with BSCR. Additional HLA-A alleles were found to be associated with BSCR, and those with the largest effects belonged to the same HLA-Aw19 broad antigen serotype group: HLA-A29:02, A30:02, A31:01 and A33:01 (FIG. 1). As a group, HLA-Aw19 alleles were significantly enriched in the second allele of BSCR patients (OR=4.44, p=2.2e-03, FIG. 2, blue bars). This result suggests, for example, that individuals carrying two copies of HLA-A29 would be at a greater risk of developing BSCR compared to those carrying one copy. It also suggests that other Aw19 allele may play a role in BSCR co-susceptibility or pathogenesis in concert with A29. The sole exception within the HLA-Aw19 serotype group is HLA-A32, which has been reported not to share the defining Aw19 binding domain (McKenzie et al., Genes Immun., 1999, 1, 120-129); HLA-A32 appears to be depleted in BSCR cases and thus protective against BSCR (OR=0.28, p=0.1).

The above results presented two issues due to the small numbers of controls in UParis (n=108): 1) The frequency of alleles might not represent the frequency of HLA-A alleles in general EUR population. 2) While the high ORs replicate in several HLA-Aw19 alleles, the numbers are not sufficient to support significant associations. To tackle these concerns, the frequency of HLA-A alleles in three other large European (EUR) ancestry control populations, two cohorts from the Geisinger Health System (GHS cohort #1, n=77,198 and GHS cohort #2, n=59,072) and the UK Biobank (UKB, n=463,315) were examined. In all three datasets, the EUR samples carrying at least one HLA-A29 allele were selected, matching the BSCR cohort: 4,014 A29 carriers from GHS cohort #1 (5.2% of all EUR subjects), 2,829 A29 carriers from GHS cohort #2 (4.8% of all EUR), and 38,543 A29 carriers from UKB (8.3% of all EUR). The frequencies of the second HLA-A alleles in these cohorts were compared to those observed in the BSCR cohort (FIG. 2, FIG. 1). The results support the enrichment of four of the five HLA-Aw19 alleles in BSCR cases, with highest increased risk for HLA-A30:02 (GHS cohort #1 OR=4.31, GHS cohort #2 OR=6.6, UKB OR=4.6) and HLA-A33 (GHS cohort #1 OR=3.4, GHS cohort #2 OR=2.8, UKB OR=4.9). When combining samples carrying the four co-susceptibility alleles A29, A30, A31 and A33, was found a highly significant enrichment in BSCR cases was found a when compared with the larger control cohorts (GHS cohort #1 p-val=1.29E-06, GHS cohort #2 p-val=1.07E-06, UKB p-val=9.62E-07, FIG. 1 top row). This analysis excludes A32 because of its biological difference in the sequence of the peptide binding domain as previously reported. The additional analyses with all Aw19 alleles including A32 showed that the enrichment in cases is reduced when it is included (FIG. 1 bottom row).

In order to test whether these associations are affected by measurable confounders, logistic regression tests were conducted to evaluate the effects of the second HLA-A allele in HLA-A29 carriers, in UParis BSCR cases compared with each control cohort, with covariates included for sex and principal components, calculated based on genetic array data for each analytic set (FIG. 3). The results were consistent with increased risk for the HLA-Aw19 co-susceptibility alleles, A29, A30, A31, and A33.

Example 3: HLA-A32 Exhibits Protection from BSCR in an HLA-A29 Positive Cohort

HLA-A32 is underrepresented in BSCR cases (3/286, ~1%) versus A29 carrier controls (4/108, 3.7%), corresponding to a nominally significant protection from risk (OR=0.28, p=0.1; FIG. 1). When compared with the larger control cohorts, the trend protection is maintained with both UKB controls (3.4%, OR=0.3, p=0.02) and GHS controls (cohort #1: 3.8%, OR=0.27, p=0.01; cohort #2: 3.7%, OR=0.27, p=0.02). While nominally significant, this result does not pass the threshold of multiple test correction (p=3.57e-03) and will need to be further validated with additional case cohorts.

Example 4: ERAP2 is Independently Associated with BSCR

All variants and gene burdens were tested for association with case-control status, while controlling for sex and ten principal components, using a generalized linear mixed model (SAIGE). Due to the fact that both cases and controls were A29 allele carriers, the expected strong HLA-A signal was at least partially controlled, as evidenced by the strongest HLA p-value=8.98E-07, compared with p=6.6e-74 with 125 cases in the previous BSCR report (Kuiper et al., Hum. Mol. Genet., 2014, 23, 6081-6087). Overall, no locus passed the genome wide significance threshold (p<5e-8). Other than the remnant signal at HLA-A, only the ERAP1/ERAP2-LNPEP locus on chromosome 5 showed an association with disease at p<1e-6 (FIG. 2).

The previously reported top association for BSCR at this locus tags a common variant near ERAP2/LNPEP, rs10044354. This reported risk allele is in a strong linkage disequilibrium (D'=0.99, $R^2$=0.76), with a strong eQTL increasing ERAP2 expression. The results show a nominal association of rs10044354 with increased risk for Birdshot (OR (95% CI)=1.55 (1.13-2.11), p=5.8e-3). Furthermore, no significant evidence was found for an interaction of rs10044354 with rs27432-rs2287987 haplotypes (conditional haplotype test p=0.46).

Next, a meta-analysis of the results with the published results from Kuiper et al. was carried out, which yielded genome-wide significant associations for ERAP2 (rs10044354, OR (95% CI)=1.95 (1.55-2.44), p=6.2e-09) loci with BSCR (FIG. 1). Both previous and current studies showed consistent directionality for ERAP2, which, separated by over 201,222 bp, show low linkage disequilibrium (LD) in the present cohort (R2=0.18, D'=0.79).

The expression of ERAP2 has been previously reported to be disrupted by a common splice region variant (rs2248374, AF=0.53) that causes mis-splicing of intron 10 and eventual transcript degradation via nonsense-mediated decay (Andres et al., PLoS Genet., 2010, 6, e1001157; and Coulombe-Huntington et al., PLoS Genet., 2009, 5, e1000766), and which is in high LD with rs10044354 (R2=0.8, D'=1). Thus, about 25% of the population of most ancestries (including European, AF=0.53; African, AF=0.57 and South Asian, AF=0.58) is estimated to be lacking an active ERAP2 protein. Both datasets were examined for rs2248374 associations and found that it is protective for BSCR with nominal significance in both datasets (FIG. 4). Furthermore, ERAP2-rs2248374 that disrupts ERAP2 expression is protective (OR 0.56; 95% CI [0.45-0.70]; p=2.39e-07; FIG. 5). In summary, higher expression of ERAP2 protein increases risk for BSCR and a lower expression is protective.

Figure 6:
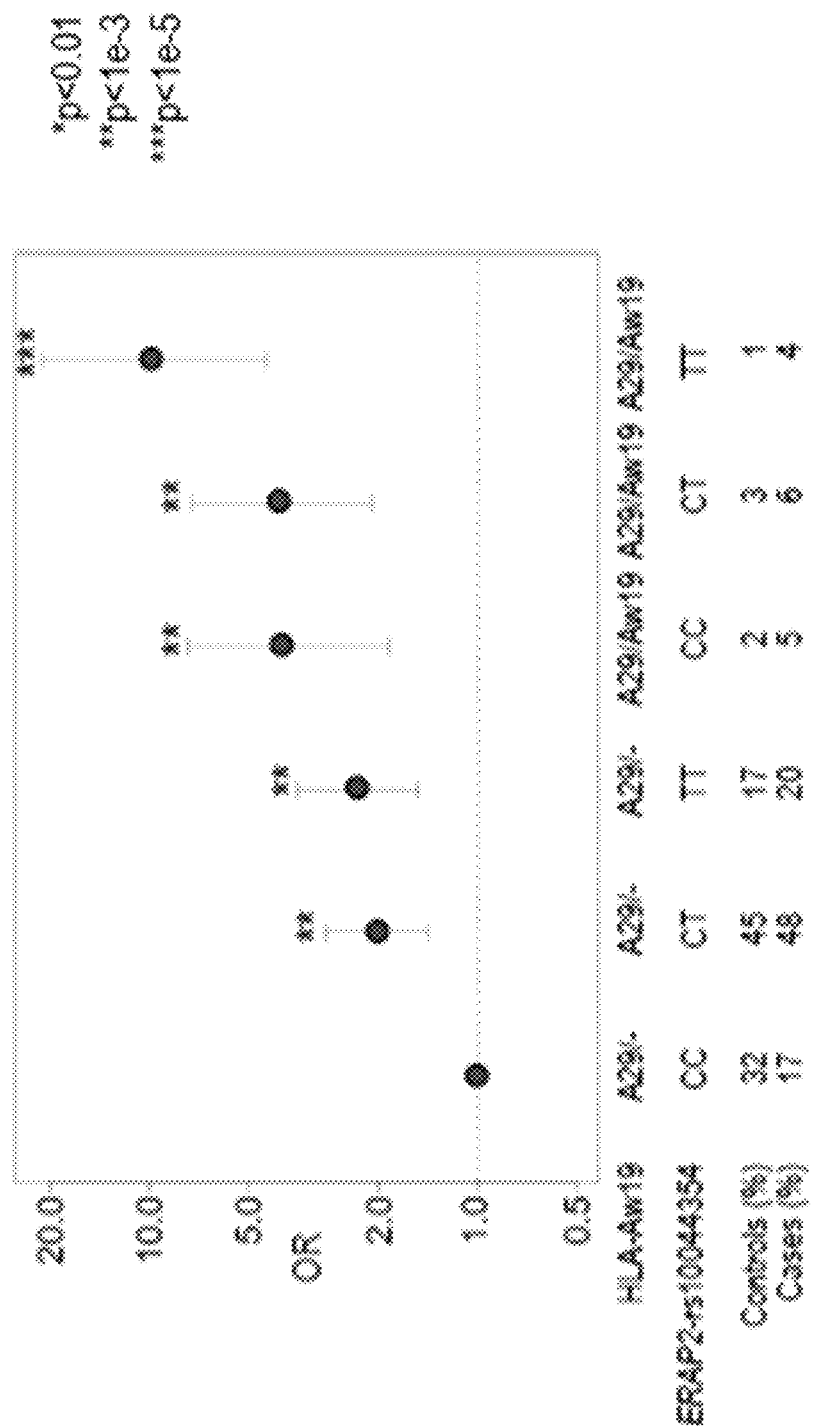
FIG. 6 shows the combined risk of ERAP2 and two copies of Aw19. Utilizing 286 Birdshot cases and 4,014 controls from GHS cohort #1 to calculate additive risk while combining risk factors in ERAP2 and Aw19. An additive genotype model of ERAP2 risk signal tagged by rs10044354 and single (A29/-) or double (A29/Aw19) Aw19 copies relative to lowest risk combination of rs10044354-CC and one copy of Aw19 allele (A29).

Example 5: Cumulative Effect of HLA-Aw19 Alleles and ERAP2 Haplotypes on BSCR Risk The potential interactions between the ERAP2 association signals and between HLA-Aw19 and ERAP2 signals was examined by calculating the cumulative effects of HLA-Aw19, and ERAP2 genotypes on BSCR risk using the 286 cases and the 4,014 A29 carriers from the GHS cohort #1. First, an analysis of ERAP2-rs10044354 risk haplotype, the top non-MHC signal in Kuiper et al. was performed, stratified by single (A29/-) versus double (A29/AW19) Aw19 background, which yielded a trend of increased risk with additional ERAP2-rs10044354-T variant alleles, particularly on the double A29/AW19 background (FIG. 6). The combination of rs10044354-TT and two copies of Aw19 with 12 cases and 34 controls was found to have the highest risk (OR=9.9 [4.4-21.2], p=1.66e-07, FIG. 7).

Example 6: Discussion

The sequencing of a new large BSCR patient cohort and HLA-A29 controls has confirmed the importance of the ERAP2 polymorphisms in increasing risk for developing BSCR. The association of the ERAP2 haplotype is consistent with a mechanism in which increased ERAP2 expression contribute to disease risk. Several studies have reported that ERAP2 haplotypes affect their expression as well as the resulting peptidome (Kuiper et al., Hum. Mol. Genet., 2018, 27, 4333-4343; Paladini et al., Sci. Rep., 2018, 8, 10398; and Sanz-Bravo et al., Mol. Cell Proteomics, 2018, 17, 1564-1577).

The present study found that several other HLA-Aw19 family alleles (HLA-A29, A30, A31, A33) contribute additional risk as the second HLA-A allele, in addition to HLA-A29 risk allele. HLA-Aw19 family alleles have a similar antigen-binding sequence and therefore would bind similar peptide motifs. Hence, the enrichment of Aw19 alleles in cases supports the inferred mechanism underlying activation of the immune response in BSCR: having two copies of these alleles may increase the cell-surface presentation of specific types of peptides in BSCR cases compared to HLA-A29 positive controls. Furthermore, it was found that the HLA-A32 allele within the Aw19 family is potentially protective.

HLA-A32 is the only HLA-Aw19 member that is found at lower rates in BSCR patients compared to controls, suggesting that it could be protective. The HLA-Aw19 serotype was initially identified by antibody binding to related family members; however, this identifies the HLA-A proteins based on structure outside of the peptide-binding groove. Serofamilies have since been re-analyzed by overall and peptide binding region sequences (McKenzie et al., Genes Immun. 1999, 1, 120-129). Comparison of the sequences in the peptide binding region reveals that HLA-A32 is more distantly related than the other Aw19 alleles which are identified as novel risk factors in this present study: HLA-A29, A30, A31, A33. When examining the differences in sequence between these Aw19 alleles, two main differences are evident: at position 9, which is part of the peptide binding domain, and a stretch of amino-acids at positions 79-83 that is only found in HLA-A32 and not the other Aw19 alleles (FIG. 8). Theoretically, the peptide pool bound by HLA-A32 would differ from the remaining members of the Aw19 family and would not activate the same subset of responding CD8 T cells. This adds further evidence supporting the hypothesis of the threshold requirement of an increased concentration of the driving autoantigenic peptide pool presented on high-risk HLA-A proteins as a driving component for development of BSCR uveitis.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

SEQUENCE LISTING

The patent contains a lengthy sequence listing. A copy of the sequence listing is available in electronic form from the USPTO web site (https://seqdata.uspto.gov/?pageRequest=docDetail&DocID=US12370257B2). An electronic copy of the sequence listing will also be available from the USPTO upon request and payment of the fee set forth in 37 CFR 1.19(b)(3).

What is claimed is:

1. A method of treating a subject having Birdshot Chorioretinopathy (BSCR), the method comprising administering to the subject an Endoplasmic Reticulum Aminopeptidase 2 (ERAP2) inhibitory nucleic acid molecule and an HLA-A29 inhibitory nucleic acid molecule.

2. The method according to claim 1, the method further comprising detecting the presence or absence of an HLA-A29 allele in a biological sample obtained from the subject.

3. The method according to claim 2, the method further comprising determining whether the subject has one or two copies of an HLA-A29 allele.

4. The method according to claim 1, wherein the HLA-A29 inhibitory nucleic acid molecule comprises an HLA-A29 antisense nucleic acid molecule, an HLA-A29 small interfering RNA (siRNA), or a short hairpin RNA that hybridizes to an HLA-A29 mRNA.

5. The method according to claim 4, wherein the HLA-A29 antisense nucleic acid molecule comprises a nucleotide sequence selected from the group consisting of SEQ ID NOs: 3871-4145.

6. The method according to claim 4, wherein the HLA-A29 siRNA molecule comprises a sense strand and a corresponding antisense strand selected from the group consisting of SEQ ID NOs: 4146-4755.

7. The method according to claim 1, wherein the ERAP2 inhibitory nucleic acid molecule comprises an ERAP2 antisense nucleic acid molecule, an ERAP2 small interfering RNA (siRNA), or a short hairpin RNA that hybridizes to ERAP2 mRNA.

8. The method according to claim 7, wherein the ERAP2 antisense nucleic acid molecule comprises a nucleotide sequence selected from the group consisting of SEQ ID NOs: 1-858.

9. The method according to claim 7, wherein the ERAP2 siRNA molecule comprises a sense strand and a corresponding antisense strand selected from the group consisting of SEQ ID NOs: 859-2748.

10. A method of treating a subject having Birdshot Chorioretinopathy (BSCR), the method comprising:
performing or having performed an assay on a biological sample from the subject to determine whether the subject comprises:
i) an HLA-A29 allele; and
ii) a functional Endoplasmic Reticulum Aminopeptidase 2 (ERAP2) protein or a nucleic acid molecule encoding a functional ERAP2 protein; and
administering to the subject a therapeutically effective amount of an ERAP2 inhibitory nucleic acid molecule and an HLA-A29 inhibitory nucleic acid molecule to the subject having the functional ERAP2 protein or the nucleic acid molecule encoding a functional ERAP2 protein, and having the HLA-A29 allele,
wherein the presence of the HLA-A29 allele and the functional ERAP2 protein or the nucleic acid molecule encoding a functional ERAP2 protein, indicates that the subject is a candidate for treating the BSCR by inhibiting ERAP2 and HLA-A29.

11. The method according to claim 10, wherein the ERAP2 inhibitory nucleic acid molecule comprises an ERAP2 antisense nucleic acid molecule, an ERAP2 small interfering RNA (siRNA), or a short hairpin RNA that hybridizes to ERAP2 mRNA.

12. The method according to claim 10, wherein the HLA-A29 inhibitory nucleic acid molecule comprises an HLA-A29 antisense nucleic acid molecule, an HLA-A29 small interfering RNA (siRNA), or a short hairpin RNA that hybridizes to an HLA-A29 mRNA.

13. The method according to claim 10, wherein the ERAP2 antisense nucleic acid molecule comprises a nucleotide sequence selected from the group consisting of SEQ ID NOs: 1-858 or wherein the HLA-A29 antisense nucleic acid molecule comprises a nucleotide sequence selected from the group consisting of SEQ ID NOs: 3871-4145.

* * * * *